United States Patent
Katz et al.

(10) Patent No.: US 11,828,741 B2
(45) Date of Patent: Nov. 28, 2023

(54) SENSOR THAT DETECTS AN ANALYTE IN THE PRESENCE OF AN INTERFERING STIMULUS

(71) Applicant: THE JOHNS HOPKINS UNIVERSITY, Baltimore, MD (US)

(72) Inventors: Howard Edan Katz, Baltimore, MD (US); Yingli Chu, Baltimore, MD (US); Hui Li, Baltimore, MD (US); Tushita Mukhopadhyaya, Baltimore, MD (US); Justine Wagner, Baltimore, MD (US); Huidong Fan, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 17/058,191

(22) PCT Filed: May 30, 2019

(86) PCT No.: PCT/US2019/034517
§ 371 (c)(1),
(2) Date: Nov. 24, 2020

(87) PCT Pub. No.: WO2019/232127
PCT Pub. Date: Dec. 5, 2019

(65) Prior Publication Data
US 2021/0156837 A1 May 27, 2021

Related U.S. Application Data

(60) Provisional application No. 62/679,413, filed on Jun. 1, 2018.

(51) Int. Cl.
*G01N 33/00* (2006.01)
*G01N 27/00* (2006.01)

(52) U.S. Cl.
CPC ......... *G01N 33/0059* (2013.01); *G01N 27/00* (2013.01)

(58) Field of Classification Search
CPC .......................... G01N 33/0059; G01N 27/00
See application file for complete search history.

(56) References Cited

U.S. PATENT DOCUMENTS 6,121,050 A    9/2000 Han
6,466,810 B1   10/2002 Ward et al.
(Continued)

FOREIGN PATENT DOCUMENTS

WO    WO-2017221714 A1 * 12/2017   ........... G01N 27/416

OTHER PUBLICATIONS

Wong, H-S., and Marvin H. White. "A CMOS-integrated 'ISFET-operational amplifier' chemical sensor employing differential sensing." IEEE Transactions on Electron Devices 36.3 (1989): 479-487. (Year: 1989).*

(Continued)

*Primary Examiner* — Robert J Eom
(74) *Attorney, Agent, or Firm* — Tarolli, Sundheim, Covell & Tummino LLP

(57) ABSTRACT

A sensor includes a first sensing element electronically sensitive to an analyte and to an interfering stimulus. The first sensing element provides a first electrical signal in response to a presence of the analyte and/or the interfering stimulus. The sensor also includes a second sensing element electronically sensitive to the analyte and to the interfering stimulus. The second sensing element provides a second electrical signal in response to the presence of the analyte and/or the interfering stimulus. A conductive link electrically connects the first sensing mechanism and the second sensing mechanism. An electrical property is measured within the sensor that is indicative of a concentration of the (Continued)

analyte based on the first electrical signal and the second electrical signal.

12 Claims, 16 Drawing Sheets

(56) References Cited

U.S. PATENT DOCUMENTS

| | | | | |
|---|---|---|---|---|
| 2002/0167003 A1* | 11/2002 | Campbell | ............ | G01N 27/414 257/40 |
| 2002/0184939 A1 | 12/2002 | Yadav et al. | | |
| 2011/0216317 A1 | 9/2011 | Marra | | |
| 2012/0325024 A1 | 12/2012 | Amo et al. | | |
| 2013/0115136 A1* | 5/2013 | Katz | ................. | H01L 27/088 257/253 |
| 2014/0099729 A1* | 4/2014 | Mershin | ............. | G01N 33/0031 422/83 |
| 2019/0293597 A1* | 9/2019 | Kato | ................. | H03F 3/45188 |

OTHER PUBLICATIONS

Coe, D. J., et al. "Model of a MEMS sensor using a common gate MOSFET differential amplifier." Journal of Physics D: Applied Physics 39.20 (2006): 4353. (Year: 2006).*

Jimenez-Jorquera, Cecilia, Jahir Orozco, and Antoni Baldi. "ISFET based microsensors for environmental monitoring." Sensors 10.1 (2010): 61-83. (Year: 2010).*

Mabeck, Jeffrey T., and George G. Malliaras. "Chemical and biological sensors based on organic thin-film transistors." Analytical and bioanalytical chemistry 384.2 (2006): 343-353. (Year: 2006).*

Besar, Kalpana, et al. "Printable ammonia sensor based on organic field effect transistor." Organic Electronics 15.11 (2014): 3221-3230. (Year: 2014).*

Feng, Linrun, et al. "Unencapsulated air-stable organic field effect transistor by all solution processes for low power vapor sensing." Scientific reports 6.1 (2016): 1-9. (Year: 2016).*

PCT International Search Report for corresponding International Application Serial No. PCT/US2019/034517, dated Aug. 15, 2019, pp. 1-7.

* cited by examiner

PARALLEL CIRCUIT

SENSOR THAT DETECTS AN ANALYTE IN THE PRESENCE OF AN INTERFERING STIMULUS

CROSS-REFERENCE TO RELATED APPLICATIONS

This application claims the benefit of U.S. Provisional Application No. 62/679,413, filed Jun. 1, 2018, entitled "SENSOR WITH INTERFERENT VAPOR DETECTION". This provisional application is hereby incorporated by reference in its entirety for all purposes.

TECHNICAL FIELD

The present disclosure relates generally to detecting an analyte in a sample and, more specifically, to a sensor that can detect the analyte in the sample in the presence of an interfering stimulus.

BACKGROUND

Certain semiconductor materials are known to be sensitive to various stimuli, such as one or more vapors. Vapors can be distinguished from one another based on the signs and magnitudes of responses since different vapors cause responses by different mechanisms (including, for example, doping, charge trapping through electron donor-acceptor interactions, charge trapping by vapor molecule dipoles, modulation of proton conductivity, semiconductor grain boundary effects, vapor molecule complexation with semiconductor receptor functional groups, morphology-dependent differences in vapor molecule transport within the semiconductor, and the like). Arrays of semiconductors with variations in the effects of these mechanisms on responses to a vapor may create patterns of responses associated that vapor and increase the specificity with which vapors are detected. This specificity can identify vapors, for example, by chemical class, by electron donors and acceptors, by proton acids and bases, and by polarity and size. An analyte vapor can be detected in a sample in this way. However, detecting the analyte vapor becomes difficult when the sample includes the analyte vapor in the presence of an interfering stimulus. For example, the interfering stimulus can be present at a much higher concentration than the analyte vapor. Water vapor, or humidity, is a common example of a high concentration interfering stimulus. Organic vapors can also be high concentration interfering stimulus in examples where industrial or vehicular emissions are prevalent.

Referencing is a technique that exposes a sensing semiconductor device to an analyte vapor in a sample, exposes a reference semiconductor device to a reference sample with the same atmospheric conditions as the sample with no analyte vapor, and compares the respective responses. While referencing can be used to detect an analyte vapor in the presence of a higher concentration interfering stimulus, the required reference sample may be difficult to create. Moreover, filtration components may be required to separate vapors entering spaces near the sensing semiconductor device and the reference semiconductor device. Thus, referencing may not be a desirable or feasible method for detecting an analyte vapor in the presence of an interfering stimulus.

SUMMARY

The present disclosure relates generally to detecting an analyte in a sample and, more specifically, to a sensor that can detect the analyte in the sample in the presence of an interfering stimulus. Using the sensor of the present disclosure to detect the analyte in the sample in the presence of an interfering stimulus is advantageous over traditional techniques (like referencing) because the sensor of the present disclosure does not require a reference sample, a filtration component, or other added complexity to detect the analyte the sample when in the presence of the interfering stimulus.

In one aspect, the present disclosure can include a sensor to detect the analyte in the sample in the presence of an interfering stimulus. The sensor includes a first sensing element electronically sensitive to the analyte and to the interfering stimulus. The first sensing element provides a first electrical signal in response to a presence of the analyte and/or the interfering stimulus. The sensor also includes a second sensing element electronically sensitive to the analyte and to the interfering stimulus. The second sensing element provides a second electrical signal in response to the presence of the analyte and/or the interfering stimulus. The sensor also includes a conductive link that electrically connects the first sensing mechanism and the second sensing mechanism. An electrical property is measured within the sensor that is indicative of a concentration of the analyte based on the first electrical signal and the second electrical signal.

In another aspect, the present disclosure can include a method for detecting the analyte in the sample in the presence of an interfering stimulus. The method includes exposing a sensor device to a sample. The sensor includes a first sensing element electronically sensitive to an analyte and to an interfering stimulus; a second sensing element electronically sensitive to the analyte and to the interfering stimulus; and a conductive link that electrically connects the first sensing element and the second sensing element. The method also includes providing, by the sensor device, an output based on an electrical property that is indicative of a concentration of the analyte in the sample based on a first electrical signal from the first sensing element and a second electrical signal from the second sensing element.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
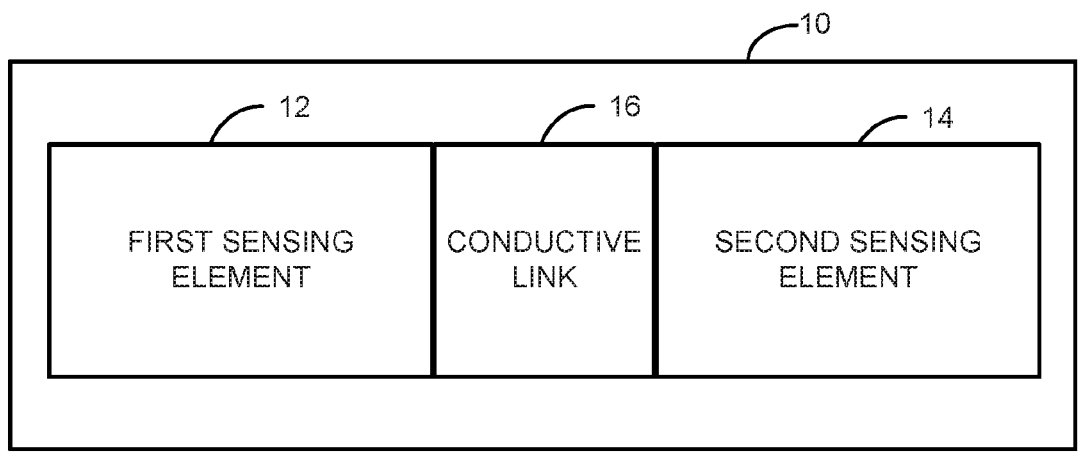
FIG. 1 is a block diagram illustration showing an example of a sensor that can detect an analyte in a sample in the presence of an interfering stimulus in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "sensor" refers to a device that detects one or more inputs from a sample. The one or more inputs can be related an analyte and/or an interfering stimuli within the sample. As an example, a sensor can include two or more sensing mechanisms to facilitate detecting the analyte in the presence of the interfering stimuli.

As used herein, the term "sensing mechanism" refers to a circuit element that includes a semiconductor material and is controlled by one or more independent variables for the detection of an analyte and/or an interfering stimulus. For example, sensing mechanisms can be arranged in a parallel configuration, a series configuration, or another type of configuration that facilitates the detection of the analyte and/or the interfering stimulus. The term "sensing element" can be used interchangeably with "sensing mechanism".

As used herein, the term "semiconductor material" refers to a solid crystalline substance having electrical conductivity between that of an insulator and a conductor. The semiconductor material can be a p-type semiconductor material, for example. The semiconductor material can be an organic semiconductor material, with an organic group like thiophene, phenylene, selenophene, benzothiadiazole, benzoxadiazole, diketopyrrole, isoindigo, etc. The semiconductor material can also include transition metal particles and/or a porogen compound.

As used herein, the term "sample" refers to an amount of a whole used for analysis. For example, the sample may be an amount of air in proximity to a sensor; however, the sample can include all of the air bounded by walls of a room.

As used herein, the term "vapor" refer to a compound that is diffused or suspended in the air. In some examples, the compound can be a gas or a suspension of material that is normally liquid or solid at room temperature.

As used herein, the term "analyte" refers to a substance being identified and/or measured. As an example, the analyte can be an analyte vapor that is being identified in a sample.

As used herein, the term "interfering stimulus" refers to anything whose presence interferes with an analyte detection procedure and generates incorrect results. An example of the interfering stimulus can include a chemical species (e.g., water vapor, an organic substance, etc.) present in a sample at a greater concentration than that of the analyte. Other examples of the interfering stimulus can include a temperature change, light, sound, pressure, magnetism, humidity, electromagnetic energy, mechanical force, etc. The terms "interfering element", "interferent", and the like, can be used interchangeably with "interfering stimulus".

II. Overview

The present disclosure relates generally to detecting an analyte in a sample. When the sample includes an interfering stimulus that overwhelms the analyte, detection of the analyte becomes difficult. The present disclosure utilizes the differing response mechanism that may pertain to the analyte and the interfering stimulus with different sensing elements. The sensor of the present disclosure does not rely on the need to minimize the response of any particular sensing element to the interfering stimulus, as has been the generally accepted goal. Instead, the sensor of the present disclosure corrects for the response to interfering stimuli through circuit design. The different sensing elements can be arranged in series, parallel, or the like, and a detection can be made that correlates to the presence of the analyte while not depending on the presence of the interfering stimuli.

As one example, the present disclosure relates to detecting an analyte vapor in air in the presence of an overwhelming interfering stimulus, like water vapor or an organic vapor. However, the present disclosure is not limited to detecting the analyte vapor in air. Instead, the present disclosure relates to detecting any analyte in any type of sample with any type of interfering stimulus.

III. Systems

One aspect of the present disclosure can include a sensor (FIG. 1) that can detect an analyte in a sample in the presence of an interfering stimulus. The sensor can include a first sensing element 12, a second sensing element 14, and a conductive link 16 that electrically connects the first sensing element 12 and the second sensing element 14. The elements of the sensor can be embodied on a substrate 10 (which can be a single substrate). The first sensing element 12 can include a first semiconductor-containing circuit element, which can include a first organic semiconductor material. The second sensing element 14 can include a second semiconductor-containing circuit element, which can include a second organic semiconductor material. Notably, the first sensing element 12 can respond differently to the second sensing element 14 with regard to the analyte and/or the interfering stimuli.

The first sensing element 12 can be electronically sensitive to an analyte and to an interfering stimulus. The second sensing element 14 can also be electronically sensitive to the analyte and to the interfering stimulus. The first sensing element 12 can provide a first electrical signal in response to a presence of the analyte and/or the interfering stimulus. The second sensing element 14 can provide a second electrical signal in response to the presence of the analyte and/or the interfering stimulus. For example, the first electrical signal and the second electrical signal can be in response to a voltage applied to at least a portion of the sensor. An electrical property can be measured within the sensor that is indicative of a concentration of the analyte based on the first electrical signal and the second electrical signal. A portion of the first electrical signal and a portion of the second electrical signal cancelling each other out in a mathematical equation (e.g., a summation, a ratio, or the like), resulting in increased selectivity in detecting the concentration of the analyte. As an example, the first sensing element 12 and the second sensing element 14 can provide a cumulative response to the analyte, while eliminating the interfering stimuli. As another example, the first sensing element 12 and the second sensing element 14 can provide a small cancellation related to the analyte, but a large cancellation related to the interfering stimuli; in this example, the concentration of the analyte is detected at a reduced amount, but the interfering stimulus is not detected.

Figure 2:
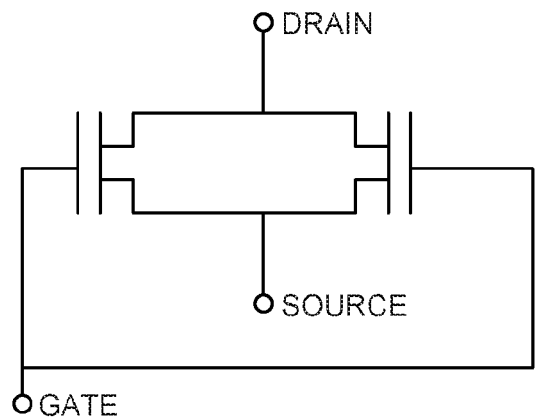
FIG. 2 is a circuit diagram showing the sensor elements of FIG. 1 arranged as a parallel circuit.
Figure 3:
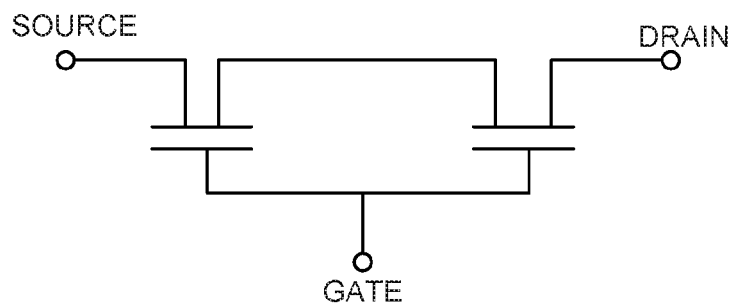
FIG. 3 is a circuit diagram showing the sensor elements of FIG. 1 arranged as a series circuit.

As shown in FIG. 2, the conductive link 16 can connect the first sensing element 12 in parallel to the second sensing element 14. As shown in FIG. 3, the conductive link 16 can connect the first sensing element 12 in series with the second sensing element. Depending on the connection between the first sensing element 12 and the second sensing element 14, the output can be changed relative to the analyte. The connection can be chosen based on the sensing elements, the interfering species, or any other factor. Additionally, the first sensing element 12 and the second sensing element 14 may include multiple parts that may individually be in series and/or parallel with each other.

IV. Methods

Figure 4:
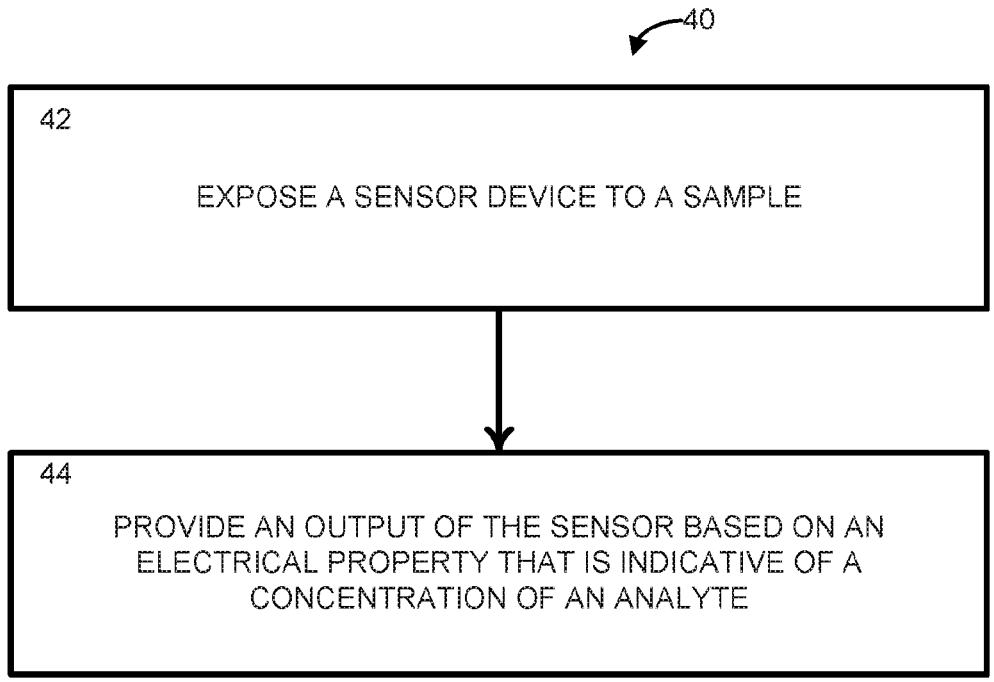
FIG. 4 is a process flow diagram of an example method for detecting an analyte in a sample in the presence of an interfering stimulus in accordance with another aspect of the present disclosure.
Figure 5:
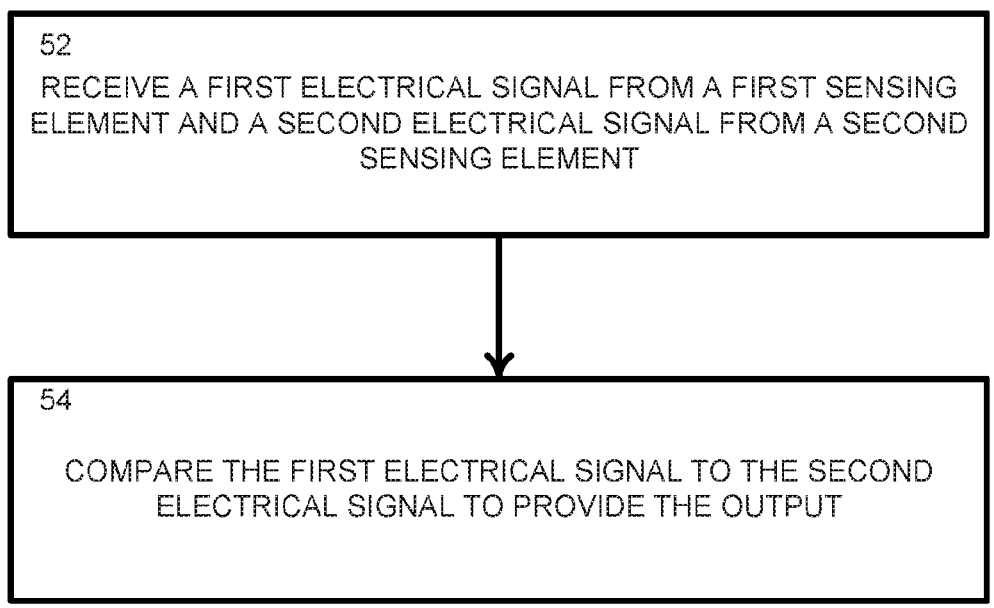
FIG. 5 is a process flow diagram of an example method for providing the output of the sensor used by the method of FIG. 4.

Another aspect of the present disclosure can include methods 40, 50 (FIGS. 4 and 5). The method 40 of FIG. 4 is directed to detecting an analyte in a sample in the presence of an interfering stimulus. The method 50 of FIG. 5 is directed to providing the output of the sensor used by the method of FIG. 4. The methods 40 and 50 can be performed using the sensor shown in FIG. 1 and described above.

The methods 40 and 50 are illustrated as process flow diagrams with flowchart illustrations. For purposes of simplicity, the methods 40 and 50 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

Referring now to FIG. 4, shows a method 40 for detecting an analyte in a sample in the presence of an interfering stimulus. At step 42, a sensor device (shown in FIG. 1) can be exposed to a sample. The sensor device includes a first sensing element (which can include at least a first semiconductor-containing circuit element, which may be a first organic semiconductor material) electronically sensitive to an analyte and to an interfering stimulus, a second sensing element (which can include at least a second semiconductor-containing circuit element, which may be a second organic semiconductor material) electronically sensitive to the analyte and to the interfering stimulus, and a conductive link that electrically connects the first sensing element and the second sensing element in series, parallel, or the like. At step 44, the sensor device can provide an output based on an electrical property that is indicative of a concentration of the analyte in the sample.

An example method 50 showing how the output can be determined is shown in FIG. 5. The output can be determined within the sensor device and may be related to properties of the sensor device, so these steps are not necessarily actively conducted. At 52, a first electrical signal can be received from a first sensing element and a second electrical signal can be received from a second sensing element. At least a portion of the first electrical signal and/or the second electrical signal can be generated in response to exposing the sensor device to the test sample. The first electrical signal and/or the second electrical signal can be related to an electrical property within the sensor device (e.g., the electrical property can be related to a circuit property, like resistance, impedance, capacitance, transconductance, or the like). The first electrical signal and the second electrical signal can be compared at 54 to provide the output. For example, at least a portion of the first electrical signal and at least a portion of the second electrical signal can cancel each other out in a mathematical equation (e.g., a ratio, a summation, or the like), resulting in increased selectivity and detecting the concentration of the analyte.

V. EXPERIMENTAL

The following example experiments ("examples") are shown for the purpose of illustration only and is not intended to limit the scope of the appended claims. Although various explanations are proposed for various observations made in the following examples, this disclosure and/or the appended claims should not be limited by or held to these explanations for the various observations.

Experiment 1

This experiment demonstrates an approach for stabilizing organic electronic devices while preserving their responses to analytes including in the presence of interfering stimuli. Two polymer organic semiconductors are used in newly designed organic field effect transistor (OFET)-based circuits with the analytes nitrogen dioxide ($NO_2$) and ammonia ($NH_3$). For this first demonstration, illumination of one semiconductor sets its drift to be the opposite of the second semiconductor kept in the dark. The circuits respond strongly to analytes, but are more stable than individual OFETs.

Methods

Device Fabrication

Two polymer semiconductors, PQT12 and PQTS12, each were synthesized and dissolved in chlorobenzene to form 4 mg mL$^{-1}$ solutions. The semiconductors were spin-coated from solutions on octadecyltrichlorosilane (OTS) treated Si/SiO$_2$ wafers at 2000 rpm for 60 seconds, followed by annealing at 120° C. for 15 minutes in a glovebox. As a bottom-gate top-contact device configuration was adopted, gold interdigital electrodes of 50 nm were thermally evaporated on top of semiconductor layer through a shadow mask.

The channel length and width are 0.2 mm and 11.0 mm, respectively. To make the circuit, a glass sheet with a length of about 30 mm and width of about 15 mm was used as substrate. PQT12 and PQTS12 transistors were placed symmetrically and fixed on the substrate with double-sided adhesive tape. Then a narrow strip of scotch tape was used to cover the space between two transistors. The two transistors were connected as a parallel circuit or a series circuit with silver paste (or gallium-indium eutectic).

Device Characterization

UV-vis spectra of PQT12 and PQTS12 films were recorded on an UV-vis spectrophotometer. The electrical performances of the transistors and circuits were carried out with a Keithley 4200 Semiconductor Parameter Instrument in ambient air. For stabilizing PQT12-PQTS12 circuits with compensatory light, a white light emitting diode (LED) was employed, from which the light intensity can be adjusted. Weighing paper was also used as a filter for minor adjustments of light intensity by covering the glass window of the testing chamber and further reducing the light intensity. Before employing for $NO_2$ detection, the circuits would be stabilized during the cyclic transfer curve test. The light was illuminated from the top side of the circuit and the PQT12 transistor in the circuit was kept in the dark with a home-made light shading cover. At the beginning of the measurement, the lowest light intensity that the LED could emit was used. After measuring the first transfer curve, the second transfer curve was tested subsequently to examine if it could match the first one well. If there was an obvious increase (or decrease) in current, the light intensity would be increased or decreased and then the transfer curves were tested again. The light intensity was adjusted until the latest transfer curve matched the previous one well and no obvious current shift was observed. After that, ten cyclic transfer curves were procured to examine if they all overlapped as one curve and further make sure that the circuit was operational stable with compensatory light. The value of required light intensity may vary from one device to another because of electrical performance nuances between these devices, and the intensity of compensatory light was in a very narrow range between 3-6 $\mu W/cm^2$.

A home-made gas flow chamber was used for exposing the circuits in an $NO_2$/air atmosphere. The desired concentration of $NO_2$ was controlled with the Environics 4040 Series Gas Dilution System. After the exposure to $NO_2$, the circuits were transferred to the testing chamber as fast as possible (on the order of one minute). The control circuits were stored in air for the same time intervals as the exposure time for the sensing circuits. To demonstrate the reproducibility and universalness of this approach, the $NH_3$ sensing test was performed in another home-made chemical sensing chamber in another lab with a similar setup. However, the sensing tests were performed by "in vivo" measurement, the sensors were kept in the chamber, with the output current recorded continually over time.

Results

Characterization of Individual PQT12 and PQTS12 Transistors

Figure 6:
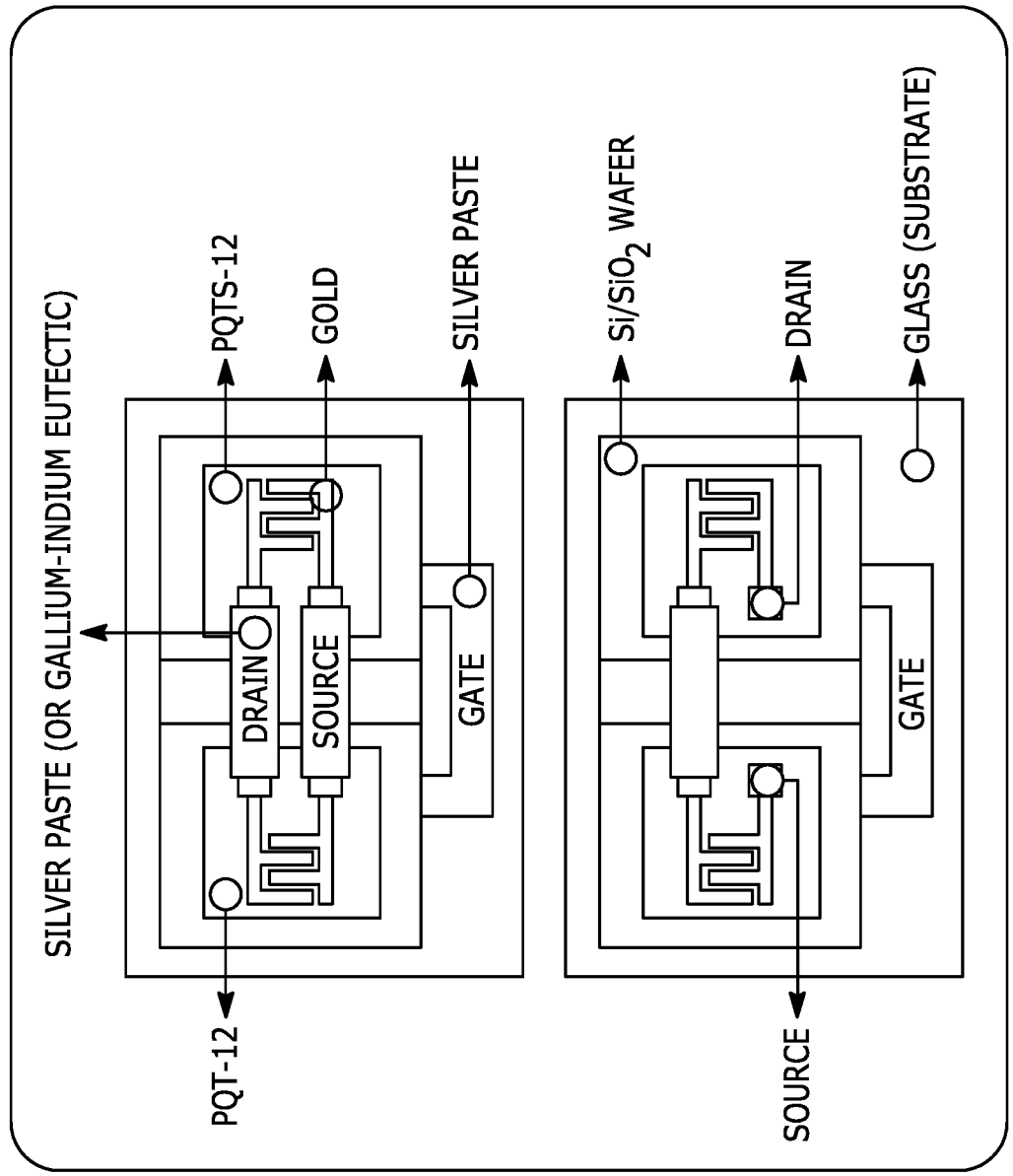
FIG. 6 shows a schematic diagram of a configurations of parallel and series circuits of PQT12 and PQTS12 transistors.
Figure 7A:
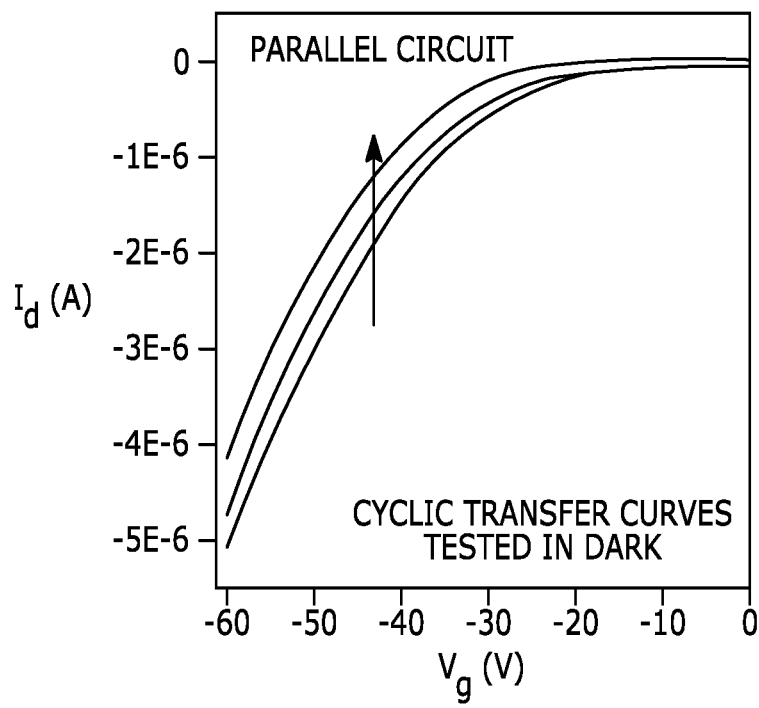
FIG. 7 shows IV plots for parallel and series circuits tested in dark and under compensatory light.
Figure 7B:
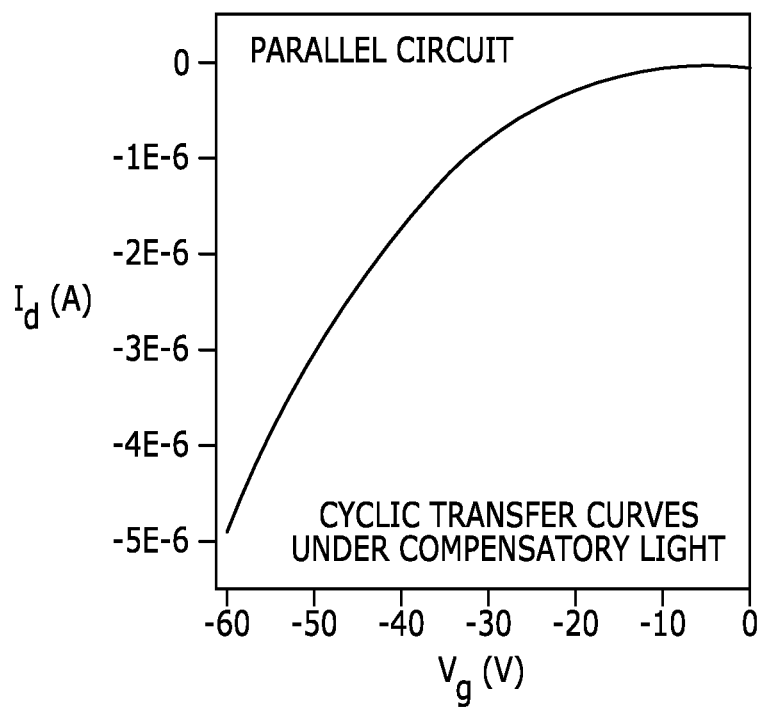
Figure 7C:
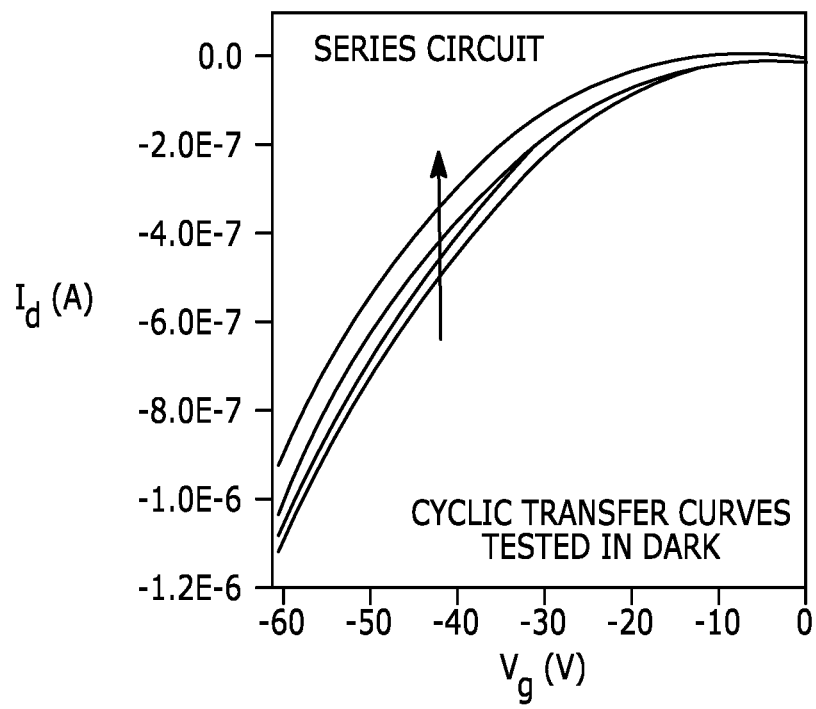
Figure 7D:
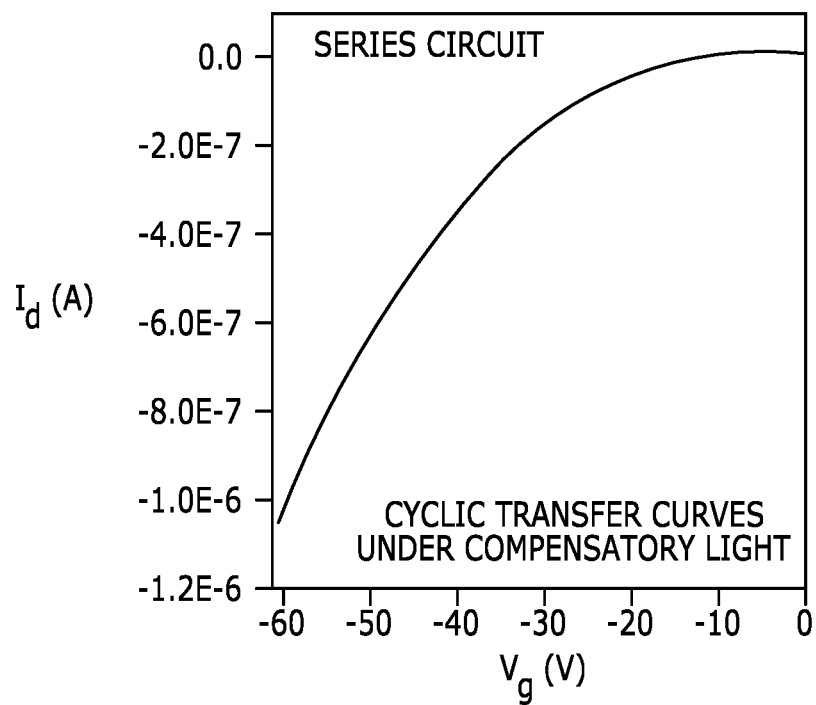
Figure 8A:
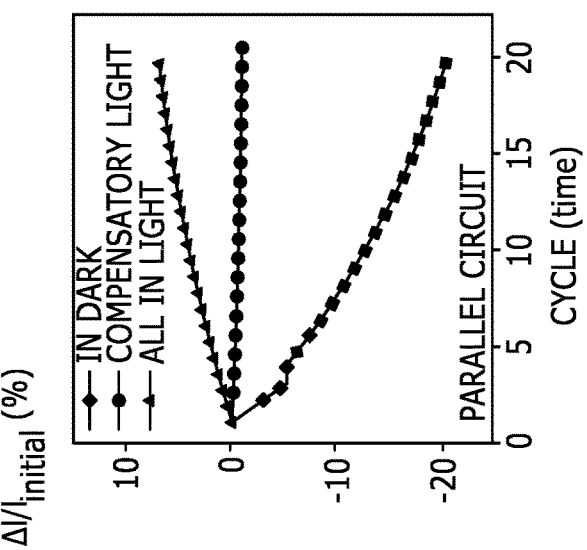
FIG. 8 shows plots for parallel and series circuits tested under different light conditions.
Figure 8B:
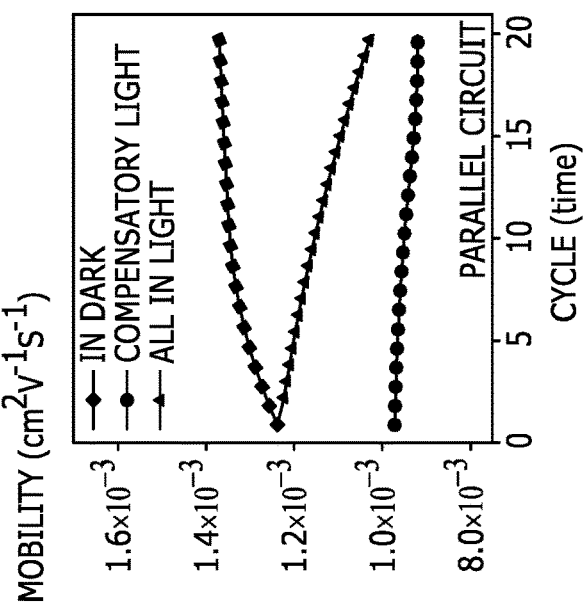
Figure 8C:
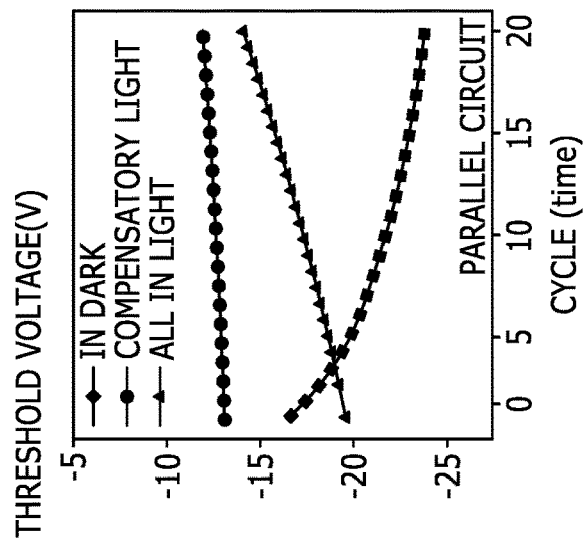
Figures 8D, 8E, 8F:
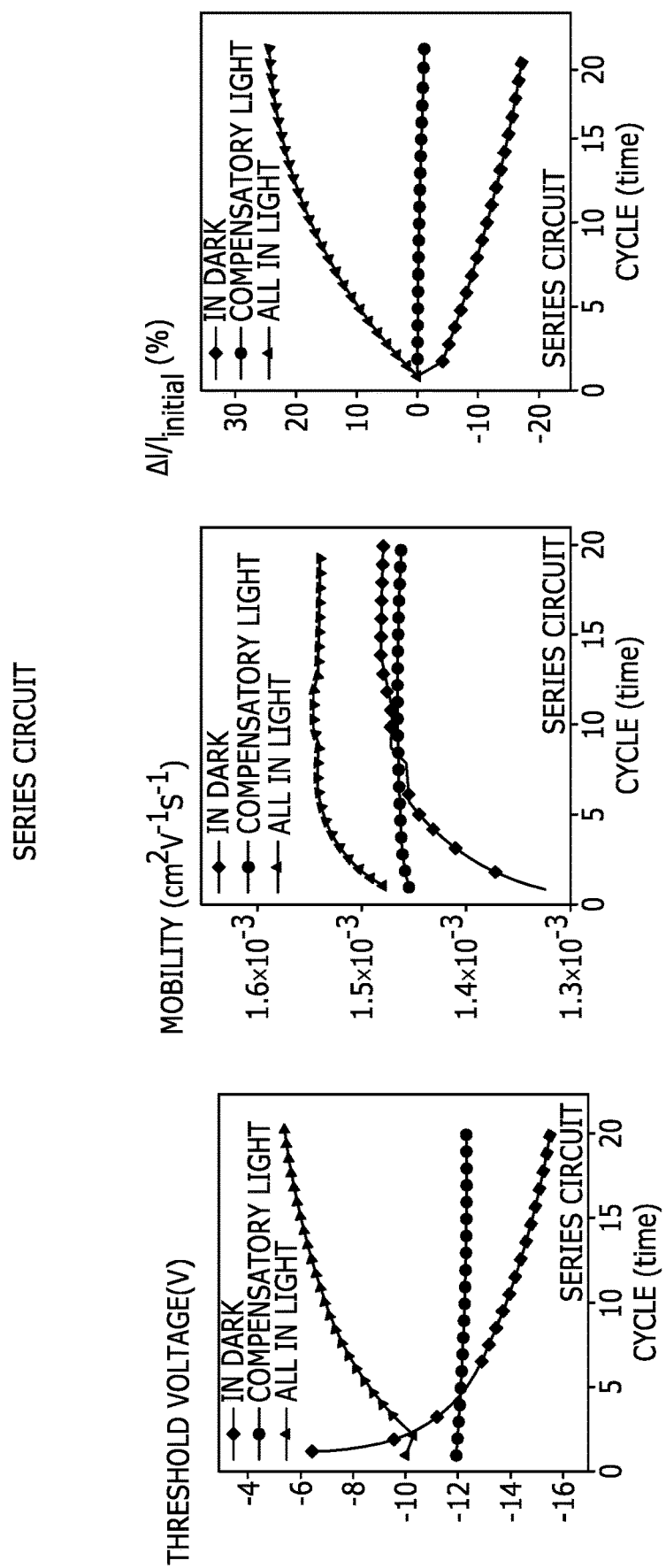
Figure 9A:
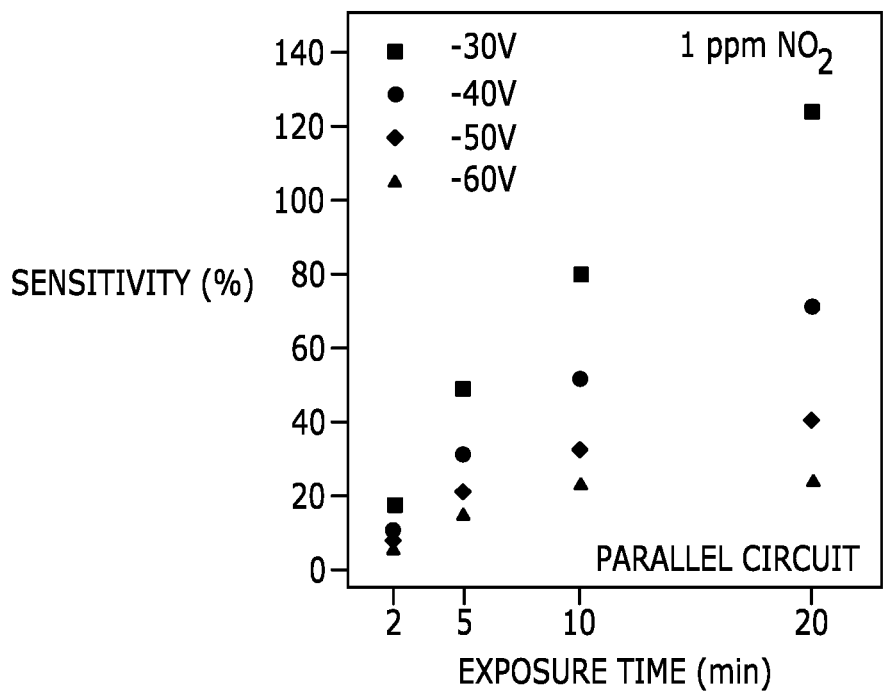
FIG. 9 shows plots of sensitivity with exposure time of parallel and series circuits.
Figure 9B:
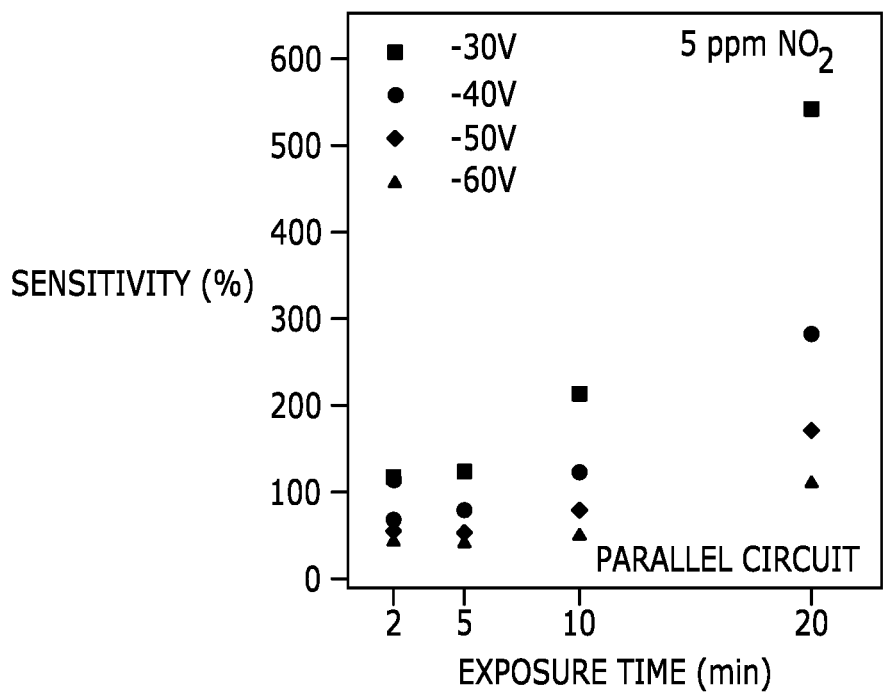
Figure 9C:
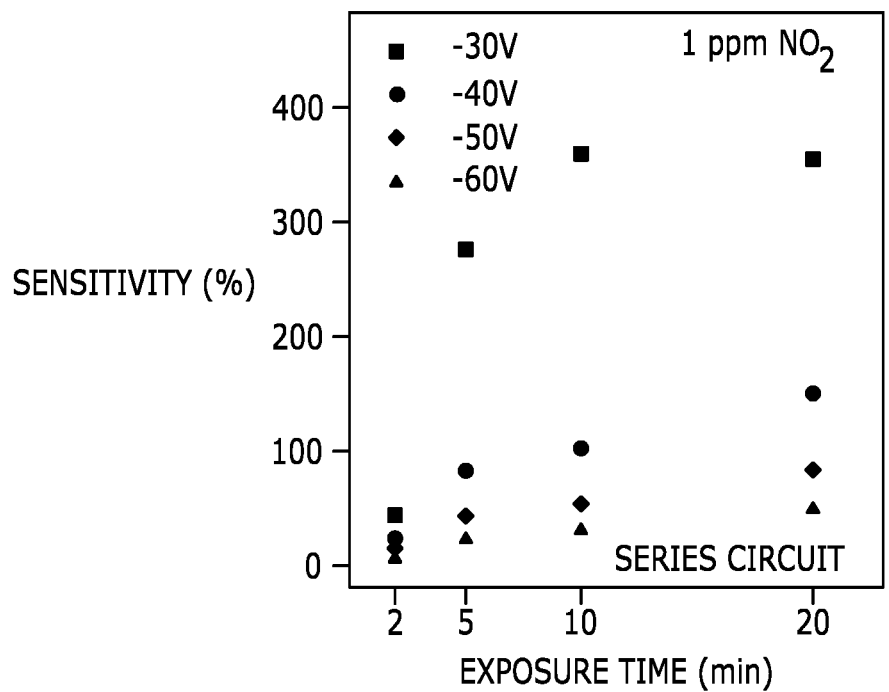
Figure 9D:
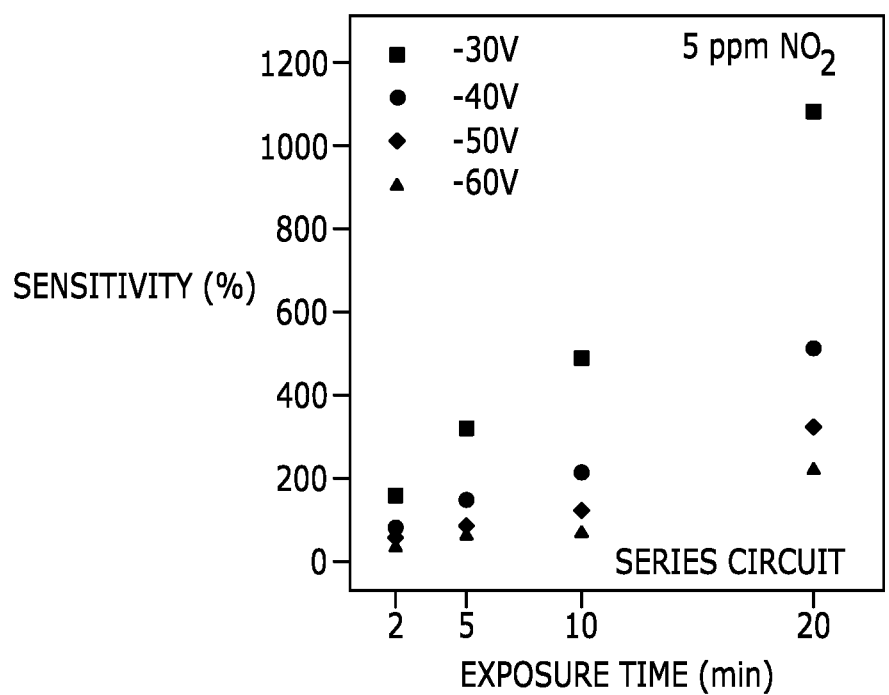

The molecular structures of PQT12 and PQTS12 are such that the two polymers share the same thiophene-based backbone while PQTS12 contains sulfide groups adjacent to thiophene rings and PQT12 does not. Both are air-stable compositions, though PQTS12 is more easily oxidized (doped) by oxidizing agents. The two semiconductors were integrated into one circuit as in the schematic diagram shown in FIG. 6. The two transistors face each other and share a common gate electrode (however, it should be noted that the gate electrode need not be shared). To investigate if the configuration has an impact on the circuit characteristics, both series and parallel connections were examined. The parallel and series circuit diagrams are shown in FIGS. 2 and 3, respectively. In a parallel circuit, the source and drain electrodes of the two transistors are connected, respectively, as a common source electrode and a common drain electrode. In a series circuit, one electrode of each transistor is connected to each other, and one of the unconnected electrodes is the source electrode while the other one is the drain electrode. Before testing the circuit, the electrical characteristics of PQT12 and PQTS12 transistors were investigated individually.

When PQT12 and PQTS12 transistors were operating in the dark, their threshold voltages drifted to negative values. This is consistent with device degradation, where normally mobile charge carriers become trapped in the semiconductor or at the interface between semiconductor and dielectric. The trapped carriers do not contribute to the current, but they are part of the electrostatic response to the gate voltage. To achieve the same mobile charge carrier concentration and turn the transistor to the ON state, a higher gate voltage needs to be applied; the threshold voltages are thus shifted. This kind of shift is reversible, and this recovery can be induced by exposing to above band-gap light. When PQT12 and PQTS12 transistors were operated under light, the electrons from photogenerated hole-electron pairs could combine with the trapped holes, leaving mobile holes in the conducting channel, thus resulting in a positive $V_{th}$ shift.

The PQT12 and PQTS12 transistors had $V_{th}$ shifts of the same sign when measured under the same lighting, while their mobilities changed in opposite directions. There are two kinds of traps at the surface of organic semiconductors: deep traps controlling $V_{th}$; and shallow traps limiting charge carrier mobility. Photogenerated holes that lead to a positive $V_{th}$ shift can also fill interfacial shallow traps; thus the mobility increases. On the other hand, besides combining with the trapped holes, the electrons from photogenerated hole-electron pairs can also act as extra shallow traps to slow the hole transport in the channel, leading to a decrease in mobility. The two opposite change tendencies affect the charge carrier density simultaneously. Thus there is a possibility for both the increase and decrease in mobility. The mobility of the PQT12 transistor had a slight decrease because of device degradation when operating in the dark. When the PQT12 transistor was operated under light, the slight increase in mobility was attributed to light-facilitated carrier transport. Compared with PQT12, two more sulfur atoms in each PQTS12 molecular unit and smaller grains and numerous grain boundaries in the thin film led to a higher trap density, and therefore a decreased mobility of the PQTS12 transistor. PQTS12 is somewhat more sensitive to moisture and oxygen. The increase of mobility when PQTS12 transistor operated in the dark indicated that there were some gases in air that facilitated the carrier transport in the short term. In the long term, the OFETs would degrade with mobility decreasing anyway. When the PQTS12 transistor operated in light, the extra shallow traps induced by photogenerated electrons slowed the carrier transport and the mobility kept decreasing.

Characterization of Light-Regulated Circuits

After PQT12 and PQTS12 transistors were integrated into one circuit, the circuit also operated in its entirety as a typical p-type transistor. At the same gate bias voltage and source-drain voltage ($V_d$) applied to the circuits, the parallel circuit usually exhibited a higher drain current ($I_d$) than the series one. The two transistors in a circuit operated at the same common gate bias, and $V_d$ across the parallel circuit was the same voltage across each of them while $V_d$ across the series circuit was the sum of the voltages across each transistor, which means both transistors in a series circuit operated at lower source-drain voltages, resulting in a smaller drain current. The $I_d$-$V_d$ transfer characteristics of the circuits are displayed in FIG. 7. Twenty cyclic transfer curves of parallel circuit and series circuit tested in the dark are shown in the left side of FIG. 7. When the circuit was tested in the dark, the whole circuit operated without any illumination. Both the parallel circuit and series circuit exhibit a drift toward lower current, which indicates device degradation. However, when the circuit operated under compensatory light, which means (unless otherwise indicated) that the PQT12 transistor in the circuit still operated in the dark while PQTS12 transistor operated under illumination with some certain light intensity that can make the whole circuit operationally stable, there was almost no current drift observed and the twenty cyclic transfer curves overlapped as one curve as shown on the right side of FIG. 7. Both the parallel circuit and series circuit could achieve operational stability with compensatory light regulation.

FIG. 8 indicates the comparison of the circuits' electrical parameters measured under different light conditions. Threshold voltages of the circuits had opposite drifts when tested in the dark and under light, just as the individual OFETs did. When the devices operated under compensatory light, the $V_{th}$ positive shift from the PQTS12 transistor and the $V_{th}$ negative shift from the PQT12 transistor offset each other, resulting in almost no $V_{th}$ shift in the circuits. The mobility change of the circuits under different light conditions is dominated by the PQTS12 transistor. (Note that "mobility" here refers to the fitting parameter that would apply to the $I_d$-$V_d$ relationship of the circuit, not a property of either material.) The increase in mobility (in the dark) may be attributed to some gases in air facilitating charge carrier transport in the short term, and the decrease in mobility attributes to extra shallow traps induced by photogenerated electrons. The opposite changes in mobility could cancel each other out, thus a much smaller shift was observed when the circuits operated under a compensatory light rather than in the dark or totally under light. Though the mobility change of the series circuit measured in light was not monotonous, which had a rapid increase first and then decreased slightly, it could be attributed to the competition between effects induced by gases in air and by photogenerated excitons. The change in current induced by the environment was also minimalized through regulating the light illuminated on the circuits. Considering all the results and discussion above, applying compensatory light to the OFET is an effective method for improving the operational stability of OFET based circuits. For the most stable circuit we have tested, the mobility increased by only 1.9% and the threshold voltage shifted within 0.4 V after sixty cyclic transfer curves were tested. With this much improved operational stability, the circuits could be desirable as gas sensors in air.

Light-Regulated Circuits for $NO_2$ Detection $NO_2$ is one of the most common air pollutants and has harmful effects on human health and the environment when its concentrations reach the 1-10 ppm range, where the sensing and detection of $NO_2$ become essential and urgent. The sensing performances of the circuits were investigated by exposing the circuits to different concentrations of $NO_2$ in air with different exposure times. All the circuits exhibited significant increase in drain current ($I_d$) after exposure to $NO_2$, due to the semiconductor polymers being oxidized (doped) by $NO_2$. Change in $I_d$ was used to calculate the sensitivity of the circuit sensors, following the formula $(I_{d,NO2}-I_{d,air})/I_{d,air}*100\%$, where $I_{d,air}$ and $I_{d,NO2}$ are the drain currents before and after exposure to $NO_2$, respectively. Both parallel and series circuits demonstrated increasing sensitivity with increasing $NO_2$ concentration and exposure time. Meanwhile, these circuit sensors achieved higher sensitivity under lower gate voltage, which might be explained as the carriers from $NO_2$ doping dominated charge transport at lower gate voltage while gate bias induced carriers dominated charge transport at higher gate voltage.

FIG. 9 plots the responses of the circuits with gate voltages of −30, −40, −50 and −60 V, which have less noise from instability than with gate voltages near the threshold voltage. Each data point is the average value from four to seven circuits. The series circuits (bottom of FIG. 9) show an obviously higher sensitivity than the parallel circuits (top of FIG. 9) under the same exposure condition. With gate voltage of −30 V, the sensitivity of parallel circuits can reach to about 550% after exposure to 5 ppm $NO_2$ for 20 min (as might be done for dosimetric monitoring) and that of series circuits can be as high as 1000% or more under the same conditions, which are outstanding sensitivities among polymer semiconductors interacting with $NO_2$. Even after exposure to 1 ppm $NO_2$ for just 2 min, the parallel and series circuits exhibited sensitivity of about 20% and 50%, respectively, which is also promising for detecting even lower concentrations of $NO_2$. High sensitivities of semiconductor thin films to $NO_2$ were previously reported, however, their baselines during detecting have shown non-negligible shifts, which are likely to result in large and uncertain noise. For example, when a device based on a hybrid semiconductor thin film was employed to detect the dynamic response to 0.3 ppm $NO_2$, the baseline showed a drift (change in current) around 10% to 20% for each test cycle, and the absolute response to $NO_2$ also kept increasing with test cycle. Thus the device operated with poor operational stability and the "real" response to $NO_2$ can hardly be defined. Besides, all tests of $NO_2$ detection in these references were taken in dry air or nitrogen to eliminate the effect of moisture on the organic semiconductors. For the OFET circuits in this work, all the $NO_2$ detection tests was carried out in a typical air atmosphere (relative humidity was around 50%), and the device can still achieve excellent operational stability and negligible noise with compensatory light regulation, making the device more compatible with real operating conditions.

Figure 10A:
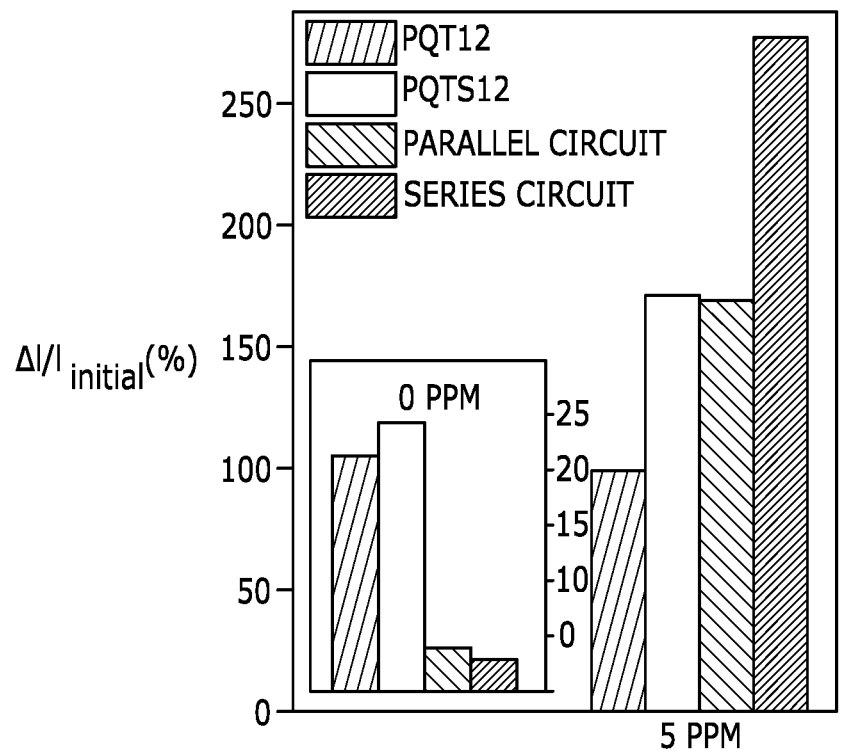
FIG. 10 shows plots of current change for parallel circuits, series circuits, and PQT12 and PQTS12 transistors.
Figure 10B:
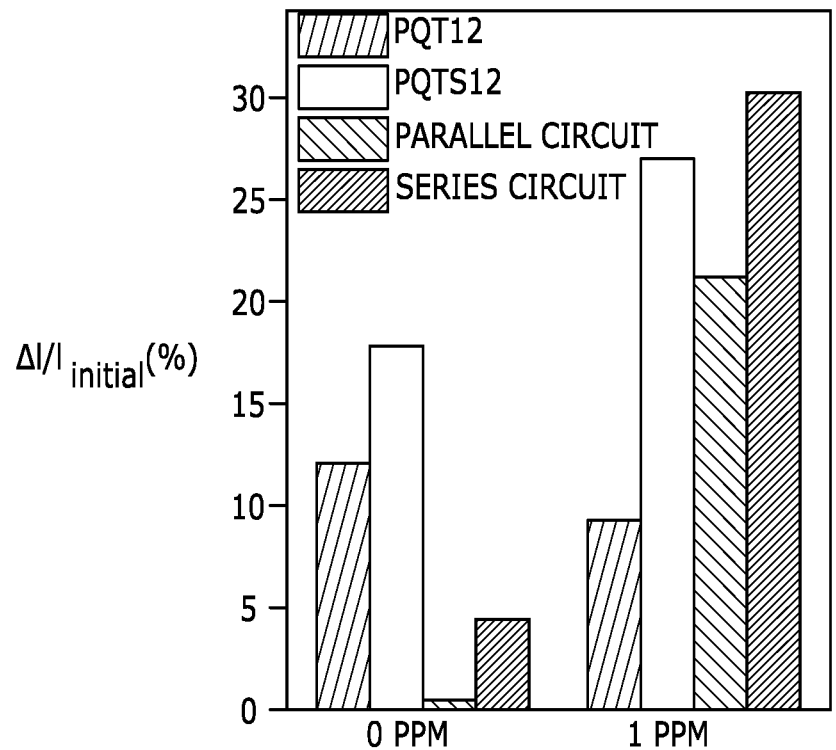

Meanwhile, to evaluate the reliability of these circuit-based sensors, the control devices were stored in air for the same time intervals as the exposure times for the sensing devices, and the ΔI was used to measure the stability of the devices as well as the noise. FIG. 10 (left side) shows the response performance to 5 ppm $NO_2$ for exposure time of 20 min (Vg=−50 V) and the insert shows the current change of control devices. Both parallel and series circuits exhibited comparable sensitivity but significantly improved stability compared with PQT12 and PQTS12 transistors from our previous work; thus the signal to noise ratios (SNRs) are dramatically increased, to 43.4 and 95.7 for parallel circuit and series circuit, respectively, while they are only 4.6 and 7.0 for the PQT12 transistor and PQTS12 transistor, respectively. When the individual transistors were used to detect 1 ppm $NO_2$ with short exposure time (5 min), the noise values (control devices stored in air as 0 ppm $NO_2$) were comparable to the response signals, as shown in FIG. 10 (right side) (Vg=−50 V). The SNRs of PQT12 transistor and PQTS12 transistor are 0.8 and 1.5, respectively, while the circuits still show higher SNRs with 70.3 for parallel circuit and 7.2 for series circuit.

Figure 11A:
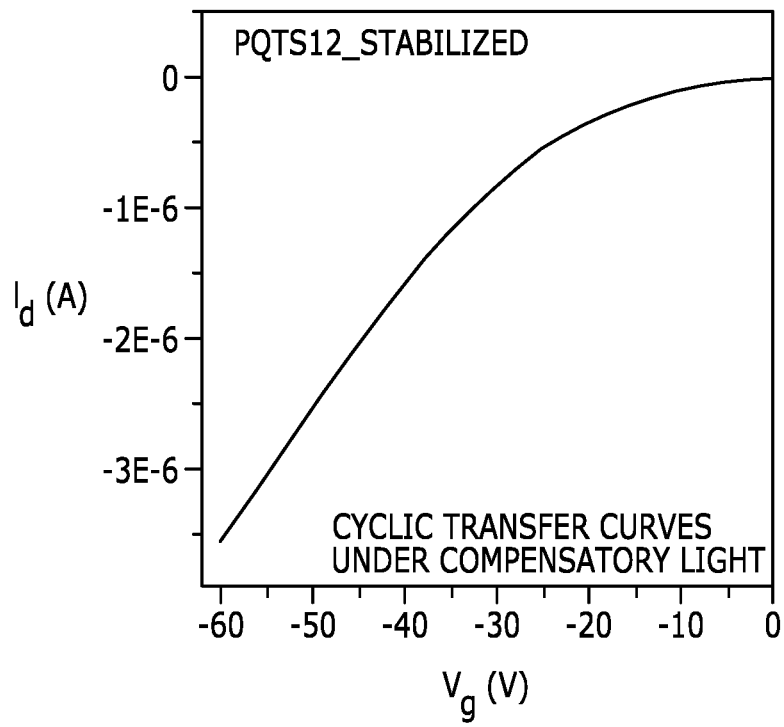
FIG. 11 shows plots related to testing of a stabilized PQTS12 transistor.
Figure 11B:
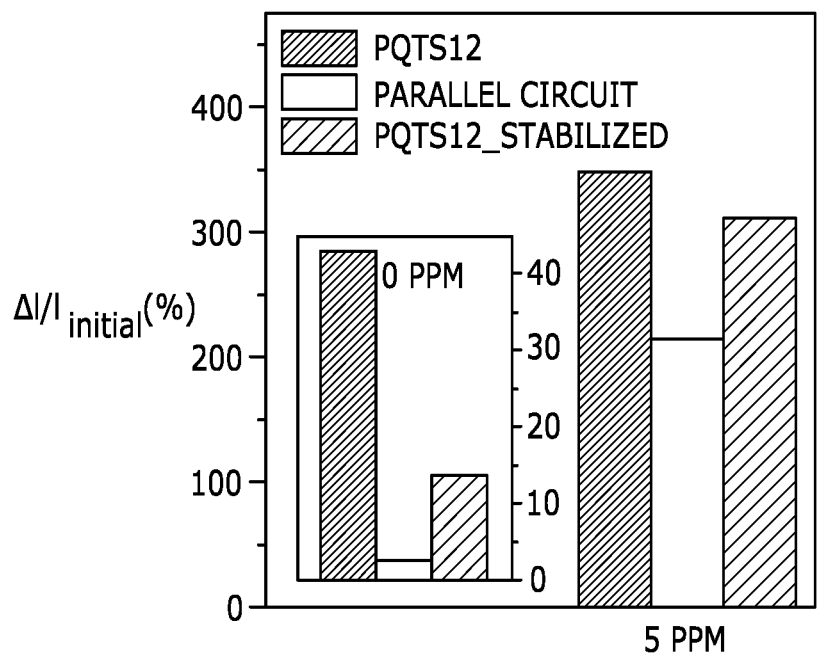
Figure 12A:
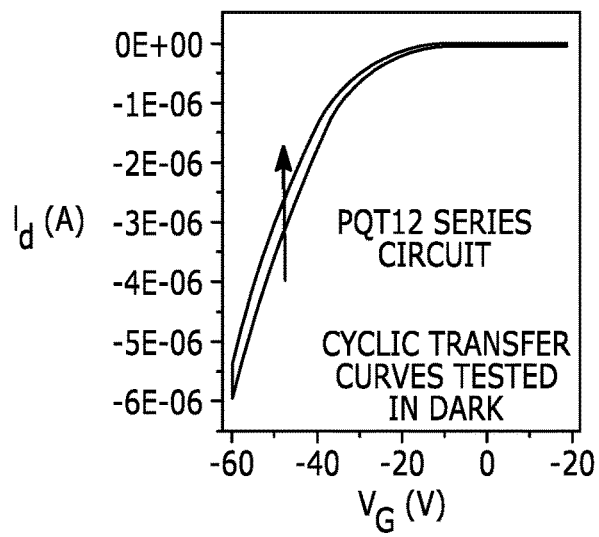
FIG. 12 shows plots related to testing of a PQT12-OFET based series circuit.
Figure 12B:
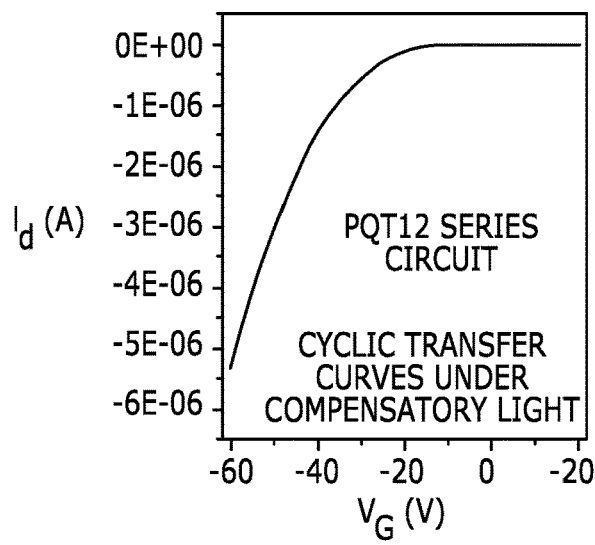
Figure 12C:
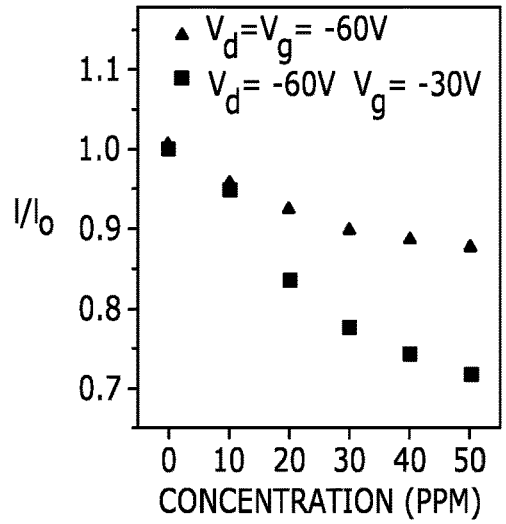
Figure 12D:
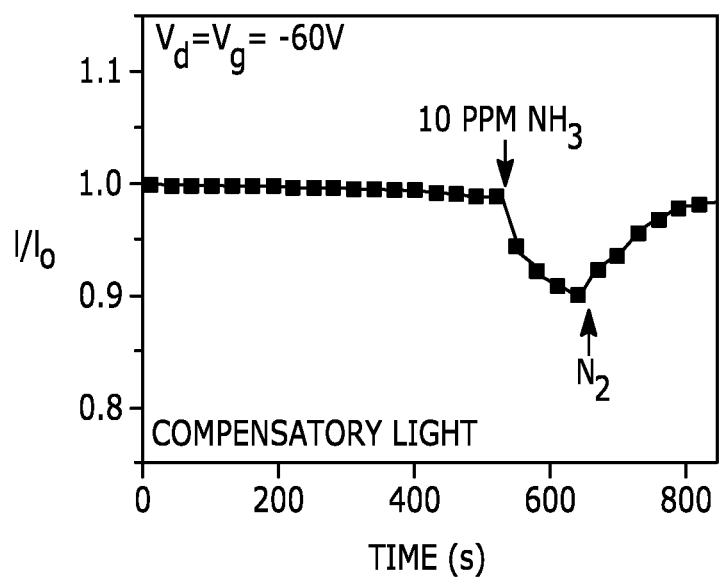
Figure 12E:
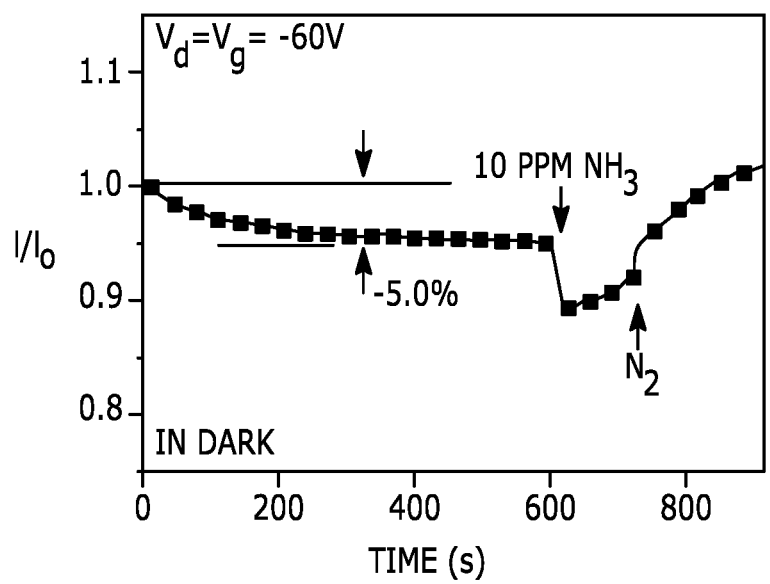

Furthermore, an individual transistor can be stabilized with compensatory light as shown in FIG. 11 (left side). Ten cyclic transfer curves of the stabilized PQTS12 OFET overlapped as one curve since photoinduced carriers and trapped carriers reached a steady state during device operation. However, this steady state in an individual transistor would not last as long as in the circuits. FIG. 11 (right side) displays the responses to 5 ppm $NO_2$ of unstabilized PQTS12 OFET, parallel circuit, and light-stabilized PQTS12 OFET. The insert (to FIG. 11, right side) shows their current change after storing in air for 10 minutes. The stabilized PQTS12 transistor shows an improved stability compared to the device without light regulation though its response to $NO_2$ is only a little smaller. The SNRs are 8.1 and 22.6 for unstabilized OFET and stabilized OFET, respectively, which indicates again that the light regulation is an effective method to achieve device operational stability and reliability. The parallel circuit shows smaller sensitivity than the both the unstabilized OFET and the stabilized OFET, while it is the most stable device in air since the companion PQT12 OFET in the circuit contributes to the stabilization. Thus the SNR of the parallel circuit is 82.8 and the highest among the three kinds of OFET based sensors.

near the non-saturation regime where the drain current was smaller than that of the transistor operated in saturation regime. The current across the series circuit was smaller than that across the parallel circuit, as we discussed before. Furthermore, the leakage current would be a non-negligible contribution to the $I_d$ in the series circuit while the $I_d$ would be much larger than the leakage current in the parallel circuit, when these circuits operated with a low gate bias fixed at −30 V. The change in current largely came from the leakage current and thus the control series circuits show considerable instability in Table 1. The stability of series circuits improves gradually with gate bias increasing. The percentage current change of the series circuit is almost the same as that of the parallel circuit, as a result of increased gate bias inducing increased drain current and the leakage current becoming negligible. Therefore, both the parallel circuit and the series circuit with light compensation achieved dramatic improvement in stability. Leakage current could be decreased further by careful patterning of semiconductors and electrodes, which so far has only been done using manual and shadow mask methods. Taken together, if the operational stability over wide working voltage range is needed, the parallel circuit is the preferred choice. Otherwise, the series circuit is a better choice than the parallel one if high sensitivity is preferred.

TABLE 1

Comparison of response performance for different devices ($V_g$ = −30 V).

| $NO_2$ | exposure | PQT12 OFETs | PQTS12 OFETs | parallel circuits | series circuits |
|---|---|---|---|---|---|
| 0 ppm | 2 min[a] | 29.2% ± 2.3% | 43.9% ± 1.9% | 1.6% ± 3.7% | 15.2% ± 8.2% |
| (control | 5 min | 27.9% ± 2.4% | 19.9% ± 1.6% | 1.3% ± 2.7% | 37.6% ± 9.8% |
| devices) | 10 min | 19.8% ± 1.8% | 40.3% ± 1.1% | 2.6% ± 4.8% | 26.2% ± 9.8% |
|  | 20 min | 32.6% ± 1.4% | 33.6% ± 1.3% | 1.1% ± 1.0% | 84.5% ± 78.6% |
| 1 ppm | 2 min | — | — | 17.5% ± 8.9% | 48.3% ± 5.4% |
|  | 5 min | 14.0% ± 2.1% | 42.7% ± 4.8% | 48.9% ± 18.7% | 125.0% ± 35.8% |
|  | 10 min | 31.6% ± 1.6% | 100.4% ± 5.2% | 80.0% ± 22.0% | 258.7% ± 35.4% |
|  | 20 min | 57.7% ± 5.8% | 208.1% ± 2.9% | 124.0% ± 13.3% | 354.1% ± 81.9% |
| 5 ppm | 2 min[a] | 119.8% ± 4.6% | 161.2% ± 5.6% | 117.1% ± 14.6% | 158.2% ± 56.6% |
|  | 5 min | 200.5% ± 6.3% | 314.5% ± 10.1% | 123.9% ± 19.3% | 379.9% ± 96.1% |
|  | 10 min | 293.4% ± 3.7% | 349.1% ± 1.8% | 215.3% ± 20.9% | 466.0% ± 65.4% |
|  | 20 min | 179.8% ± 3.5% | 315.2% ± 6.1% | 541.8% ± 135.3% | 1074.9% ± 180.1% |

[a]the exposure time in previous work is 3 min.

With excellent stability in air, the circuits are much more reliable sensors than the individual transistor-based sensors.

Moreover, data in Table 1 indicates that the sensitivity of the parallel circuit is comparable to or even better than that of PQT12 and PQTS12 transistors. In the case of series circuits, the situation is a little different from parallel circuits. It seems that the series circuit has not shown much improvement of stability but has exhibited the best response performance to $NO_2$ among all four kinds of devices in Table 1 (Vg=−30 V), which can be explained by analyzing the circuits. FIGS. 2 and 3 illustrate the circuit configurations of parallel connection and series connection, respectively. The two transistors in the parallel circuit shared a common gate bias, as did the series circuit. When drain voltage of −60 V was applied to the parallel circuit, both of the transistors operated in the saturation regime with this drain bias (−60 V). But in series circuits, the two transistors divided this $V_d$ (−60 V), which means the sum of the voltages applied to them was −60 V and each of the transistors operated with lower drain bias than that. This could explain that series circuits always had a higher sensitivity than the parallel ones as each transistor of a series circuit was always operating at lower working voltages. For a given gate bias, each transistor in the series circuit was much more likely to operate Standard deviations from the sensitivity of circuits are larger than those of individual transistors, which means the difference of the intrinsic electrical performance between each circuit is larger. It does not indicate that the circuit sensors are less stable than the individual transistor-based sensors. Mathematically, the standard deviation (SD) of circuits is larger than that of either PQT12 transistor or PQTS12 transistor since it is a kind of addition of SDs from both of the transistors. However, if this is the only reason for the large SD, the series circuit should have much larger numerical SD values than the parallel circuit. In the parallel circuit, two transistors operate relatively independently and the SD of the circuit is roughly the linear addition of SDs from the two devices. In the series circuit, two transistors influence each other and the SD is thus magnified. However, since the SDs of series circuit and parallel circuit have no differences in magnitude, we suggest that the higher variation of circuits than that of individual transistors mainly comes from more fabrication steps after the individual transistor fabrications have been completed, with their associated imprecisions. The undesirable defects were likely to be introduced when two individual transistors were fixed on the substrate and connected to each other with liquid metal all by hand, which could be minimized by optimizing the preparation procedure in large-scale fabrication.

Light-Regulated Circuits for NH$_3$ Detection

We also explored the selectivity of the light-regulated circuit which consists of two PQT12 OFETs in series, the more responsive configuration as discussed above. The semiconductor PQT12 is more stable than PQTS12, but also more susceptible to charge carrier quenching/dedoping because of its less facile dopability. Since NO$_2$ is an oxidizing/doping gas and augments the current of PQT12-based sensors, the reducing/dedoping gas NH$_3$, which is also a noxious gas, was selected as another analyte. Before detecting NH$_3$, the PQT12 series circuit was stabilized with compensatory light. The circuit showed a decreasing current drift in twenty cyclic transfer curves when it operated in dark (FIG. 12, top left), while all the twenty transfer curves overlapped as one when the circuit operated under compensatory light (FIG. 12, top middle). The current decrease induced by degradation of one PQT12 OFET was cancelled by light-induced current increase in the other PQT12 OFET, which is similar to the situation described in PQT12& PQTS12 circuits. With this light-regulated PQT12 series circuit, real-time responses to different concentrations of NH$_3$ was tested and variable current decrease was observed, as shown in FIG. 11 (top right). When the circuit sensor operated at high gate voltage (−60 V), the decrease in current reached saturation with low NH$_3$ concentration. When the circuit sensor operated at low gate voltage (−30 V), a higher sensitivity and a wider detection range were achieved. This gate voltage-dependent detection sensitivity was also observed in PQT12& PQTS12 circuits for NO$_2$ detection. The difference is that while NO$_2$ oxidized the semiconductor and augmented the current, the donation of lone pairs from NH$_3$ reduced the hole concentration in the semiconductor and the current decreased. This shows the distinct responses to oxidizing and reducing gases. The SNR was compared for 10 ppm NH$_3$ detection when the PQT12 series circuit operated under different light conditions. There was a negligible current drift in the light-regulated circuit sensor before NH$_3$ detection (FIG. 12, bottom left), while the noise value was comparable to the response in the circuit sensor operating in dark (FIG. 12, bottom right). The SNRs for these two sensors are 6.7 and 1.1, respectively, and after NH$_3$ was infinitely diluted with nitrogen, the light-regulated sensor was more reversible than the sensor operating in dark. These results also indicate that the compensatory light strategy is applicable to circuit sensors based on the same two OFETs.

Experiment 2

This experiment utilizes pairs of transistors with materials that show similar drifts in conductance when operated in the ordinary environment, but different responses to analytes. Thus, when assembled in series circuits, the voltage drop across each device is similar as the sensor is operated in the ordinary environment, and the drift in voltage measured as a position between the devices is minimized. When the circuits are exposed to analytes, the voltage measured at a position between the devices changes markedly, and the ratio of the voltage change with and without the analyte exposure is higher than the ratio of conductance changes measured on individual devices with and without the analyte exposure.

Materials

The Poly (3,3'''-didodecyl quarter thiophene) (PQT-12) was synthesized from 2-bromo-3-dodecylthiophene that was made via a literature procedure. A solution of 2-bromo-3-dodecylthiophene (1 g, 3.0 mmol) and DMSO (50 ml) was stirred at room temperature. 3 mol % of PdCl$_2$(PhCN)$_2$ (34.7 mg, 0.09 mmol), potassium fluoride (350 mg, 6.0 mmol) and silver (I) nitrate (1 g, 6 mmol) were added in the solution successively. The mixture was heated at 60° C. and stirred overnight. Additional potassium fluoride (350 mg, 6.0 mmol) and silver (I) nitrate (1 g, 6 mmol) were added and then the mixture was stirred for further 12 h. The final mixture was filtered through a Celite column and washed with diethyl ether. The filtrate was washed with water and the organic layer was dried over anhydrous Na$_2$SO$_4$ and concentrated under reduced pressure. The crude solid was purified by column chromatography to afford 663 mg of light yellow solid 1 (67%). $^1$H NMR (CDCl$_3$) δ 6.91 (s, 2H), 2.88-2.84 (t, 4H), 1.64-1.54 (m, 4H), 1.31-1.25 (m, 40H), 0.90-0.86 (t, 6H). FAB-High resolution Mass Spectrum: Calcd. for [M+H]$^+$: 660.69. Found: 660.20.

PQT-12 was synthesized using 5,5'-dibromo-4,4'-didodecyl-2,2'-dithiophene (300 mg, 0.45 mol) and 5,5'-bis(trimethylstannyl)-2,2'-bithiophene (223 mg, 0.45 mol), added into a Schlenk tube and subsequently dissolved in 6 mL of degassed chlorobenzene. The solution was purged with nitrogen for 10 min, and then Pd$_2$(dibenzylideneacetone)$_3$ (3 mol %) and P(o-tolyl)$_3$ (12 mol %) were added. The reaction mixture was stirred at 120° C. for 2 days. After being cooled to room temperature, the solution was precipitated in methanol and subjected to Soxhlet extraction successively in methanol, acetone, and hexane for the removal of oligomers and catalytic impurities, followed by collection in chloroform and precipitated in methanol with a yield of 71%. $^1$H NMR (Toluene-d$_8$, 100° C.) δ 7.44-6.76 (m, 6H), 2.76 (m, 4H), 1.70 (m, 4H), 1.43-1.30 (m, 33H), 0.88 (m, 6H).

Device Fabrication

The PQT-12 and polystyrene (PS) (used as the semiconductor) were dissolved in Chlorobenzene (CB) with a concentration of 8 mg/mL. Then, the PQT-12 solution was added to the PS solution (ratio 1:1) and mixture under ultrasonic agitation for 15 min. Finally, solutions were filtered with a polytetrafluoroethylene (PTFE) filter.

Figure 13:
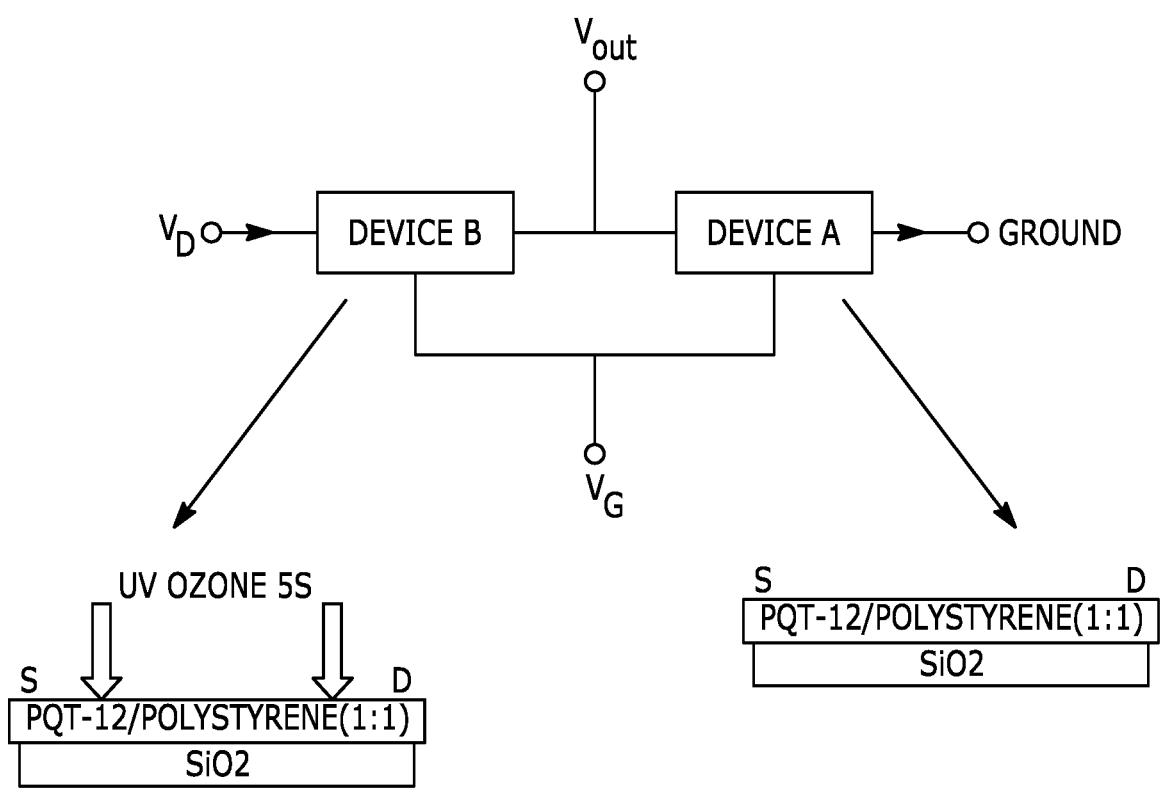
FIG. 13 is a schematic illustration of an example series circuit arrangement.

Silicon substrates (300 nm oxide) were cleaned in piranha solution, followed by deionized water (DI) and Isopropyl Alcohol (IPA) rinse. After that, the UV-Ozone cleaning was performed before the HMDS treatment (120° C., 2 h in vacuum oven). Subsequently, PQT-12/PS blend solutions were spin-coated onto the silicon wafer, the residual solvent was removed by annealing the samples on a hot plate at 120° C., then, the samples were exposed to the UV-Ozone for 5-10 s. Finally, the source and drain electrodes of 50 nm gold (Au) were thermally deposited on the blend film and patterned with a shadow mask. The length and width of the channel were 200 um and 1.1 cm, respectively. As shown in FIG. 13, the device with 0 s UV-Ozone treatment is referred as device A, and the device with 5-10 s UV-Ozone treatment is referred as device B. The UV-Ozone treatment oxidizes the transistor, making its resistance and NO$_2$ sensitivity higher, but not significantly changing its drift in the ambient environment.

Series Circuits

Device A (0 s UV-Ozone treatment) and Device B (5-10 s UV-Ozone treatment) were connected as series circuits by using Gallium-Indium eutectic. The circuit layout is shown in FIG. 13.

Electrical Characteristics Measurements

The electrical characteristics of all the devices and circuits were measured with a Keithley 4200-SCS Source Measure Unit. The gate voltage was set from 20 to −40 V and the drain voltage was set at −40 V. The OFET devices and the circuits were stored in a test chamber. Dry air and 50 ppm NO$_2$ were mixed by a mass flow controller to obtain gas concentrations delivered to the test chamber in which the electrical characteristics were measured. Exposures to each concentration of gas were three minutes in duration.

Demonstration of Stabilized Circuit with Increased Signal/Noise

Pairs of transistors were utilized with materials that show similar drifts in conductance when operated in the ordinary environment, but different responses to analytes. Thus, when assembled in series circuits, the voltage drop across each device is similar as the sensor is operated in the ordinary environment, and the drift in voltage measured as a position between the devices is minimized.

Figure 14A:
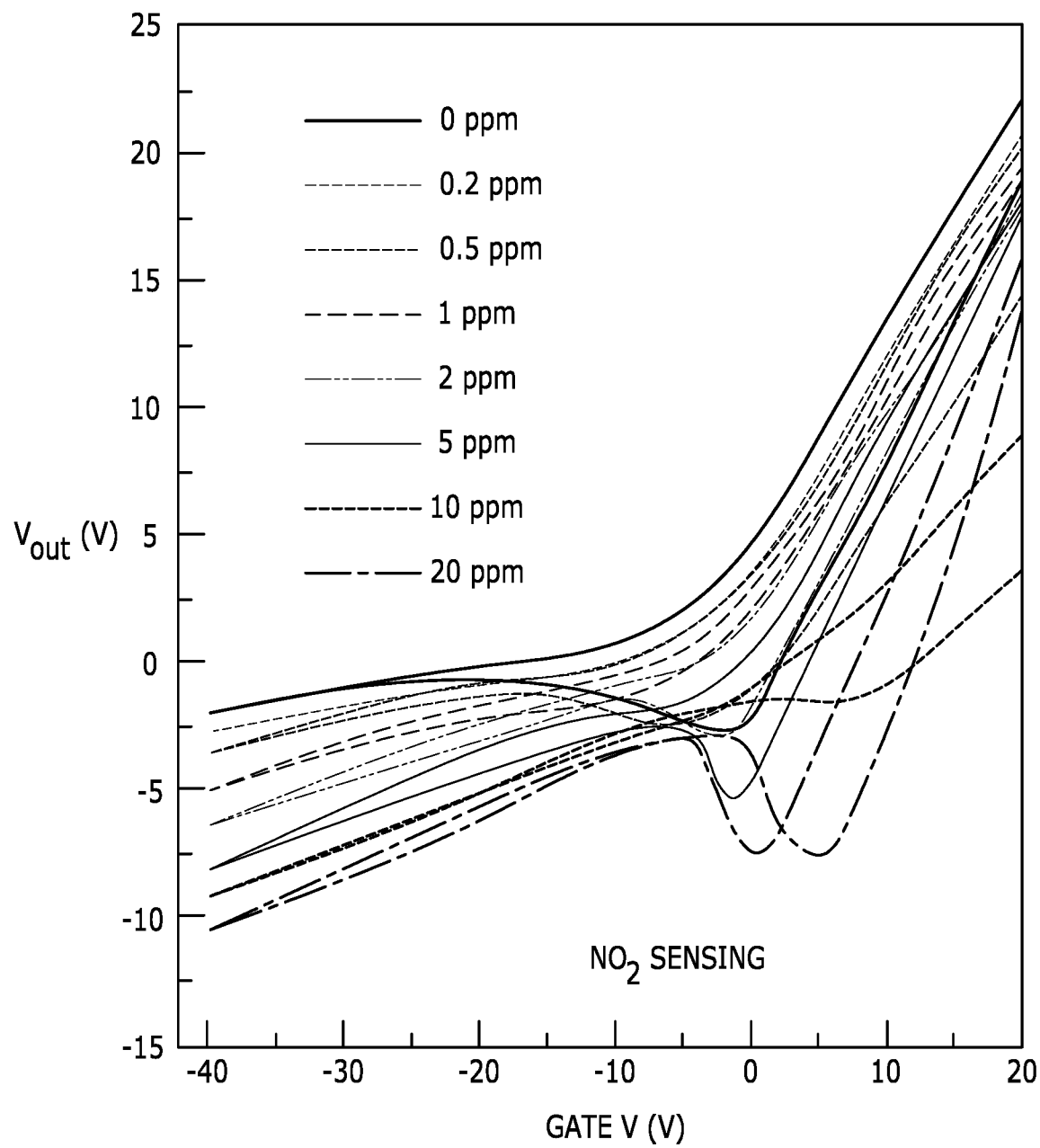
FIG. 14 shows plots comparing the output voltage of the example series circuit versus the gate voltage when in the presence of $NO_2$ and when in humid ambient air.
Figure 14B:
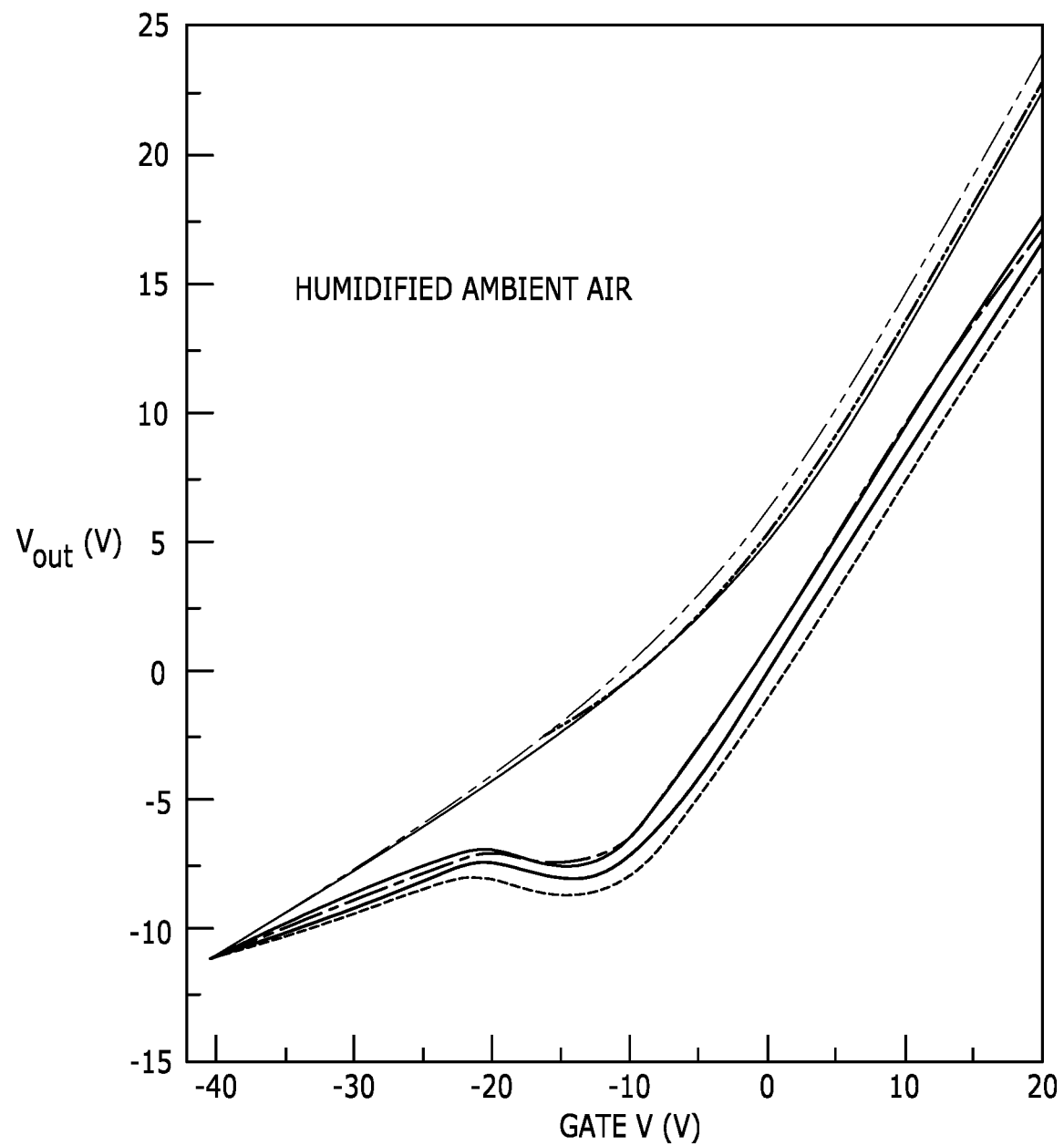

When the circuits are exposed to analytes, the voltage measured at a position between the devices changes markedly, and the ratio of the voltage change with and without the analyte exposure is higher than the ratio of conductance changes measured on individual devices with and without the analyte exposure. When linked as Device A and Device B in a series circuit, the output voltage Vout changes little in the humid ambient air (without the NO$_2$ analyte vapor) as function of gate voltage $V_G$, but responds strongly to NO$_2$ analyte vapor, as shown in FIG. 14.

Experiment 3

In this experiment, circuits are made using pairs of transistors. The materials and voltages are selected so that changes in conductances of the two transistors as a result of operation in the ordinary environment compensate each other, so the conductance drifts of the assembled circuits are decreased. Furthermore, because the responses of the transistors to analytes are different, the ratios of responses to drifts are increased in the circuits compared to the individual transistors.

Methods

Sample Preparation

Poly [3-(3-carboxypropyl)thiophene-2,5-diyl] (regioregular) and poly[3-(ethyl-4-butanoate)thiophene-2,5-diyl] (regioregular) were purchased from Rieke Metals. Before use, the polymers were individually repurified by Soxhlet extractions with methanol for 24 hours followed by hexanes for 24 hours. They were then dried under high vacuum for a full day. Afterwards 10 mg of poly [3-(3-carboxypropyl)thiophene-2,5-diyl] (regioregular) was dissolved in anhydrous N,N-dimethylformamide and sonicated for 1 hour. The mixture was then placed on an oil bath at 60° C. for 1 hr, and then 5 minutes at 105° C. The solution turned bright red and transparent. Afterwards, the hot mixture was removed from the oil bath and allowed to cool to room temperature in which the mixture turned to dark red, nontransparent solution. The solution was filtered using a hydrophilic 0.45 μm PTFE membrane. The Poly [3-(ethyl-r-butanoate)thiophene-2,5-diyl] (regioregular) (10 mg) was dissolved in anhydrous chlorobenzene and sonicated for 1 hour. The mixture was then placed on an oil bath at 60° C. for 1 hr. The solution turned bright red and transparent. Afterwards, the hot mixture was removed from the oil bath and allowed to cool to room temperature. The solution was filtered using a hydrophobic 0.45 μm PTFE membrane.

Device Fabrication

The polymers were processed over highly-doped p-type Si wafers with 300 nm of silicon thermal oxidation (University Wafer, MA, USA). Resistivity of wafers are 1-20 ohm-cm. Substrates were cleaned before usage by first dicing the wafers into 1 inch×1 inch squares, sonicating in acetone for 20 minutes, washing with distilled water, and then soaking in piranha solution (30% hydrogen peroxide in 70% sulfuric acid) for at least 4 hours. Afterwards, the substrates were washed and sonicated in distilled water for 20 minutes, dried with nitrogen, and then subjected with O$_2$ plasma cleaning for 20 minutes. Poly [3-(3-carboxypropyl)thiophene-2,5-diyl] (regioregular) in 10 mg/mL of DMF solution was spin coated onto the Si/SiO$_2$ substrate at 1600 rpm for 5 minutes with a spin acceleration rate of 100 rpm/s. Poly [3-(ethyl-4-butanoate)thiophene-2,5-diyl] (regioregular) was spun at 1600 rpm for 1 minutes with a spin acceleration of 300 rpm/s. The thickness of films are in the order of roughly 25 nm±5 nm to which a Filmetrics F20-NIR was used. The devices were then placed on a hot plate at 60° C. in a glove box overnight with no light exposure. Lastly, gold electrodes (50 nm) were thermally evaporated onto the polymer using a 2 parallel electrode strip with a channel width (W) 0.159 cm and Length (L) 0.794 cm with an active area of 12.6 mm$^2$.

Fluorene-containing polymers with conductivity decreases in ambient air:

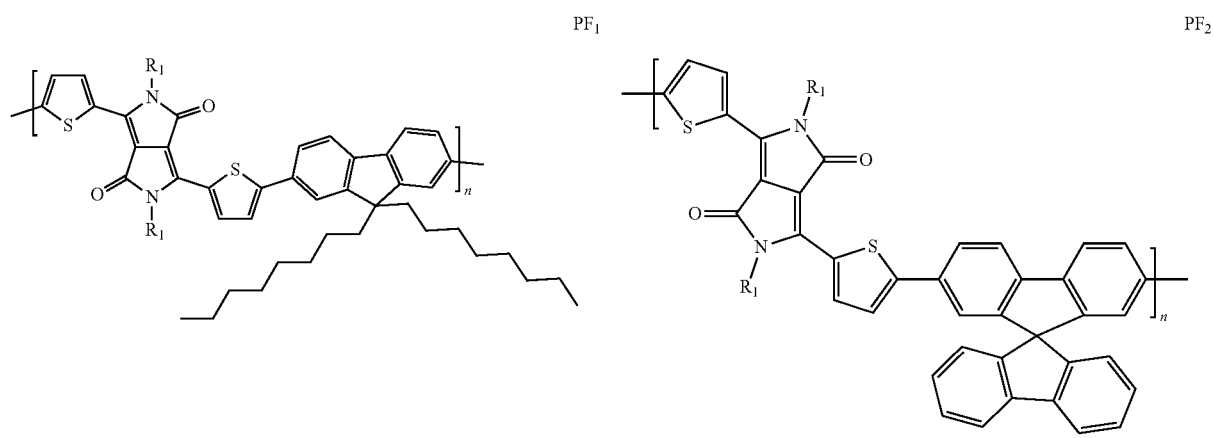

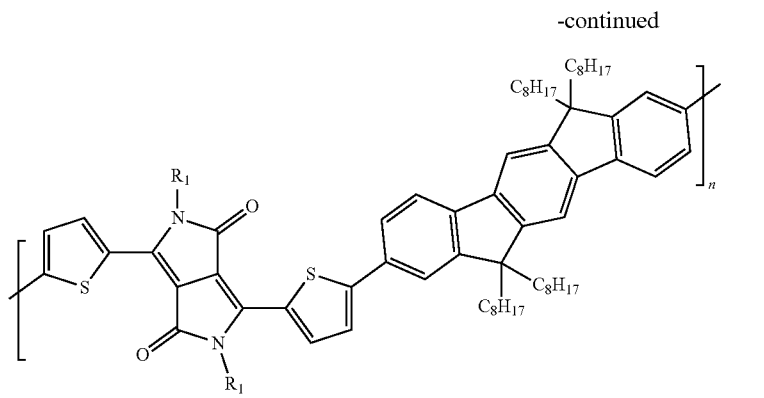

PF3

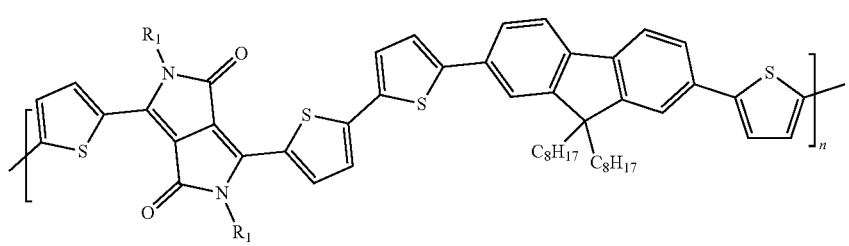

PF4

Diketopyrrolopyrrole-Fluorene Based Copolymers
(R₁=2-Ethylhexyl)

The four polymers shown above have been named as PF1, PF2, PF3, and PF4. The linear n-octyl alkyl chain-containing fluorene units have been chosen as one of the monomeric units. The polymers were synthesized by a previously reported Suzuki cross-coupling reaction/palladium (II) catalyzed C—H activation reactions involving appropriate monomers having boronic ester or dibromo functionalities in the presence of active ligand P(o-tol)$_3$ or pivalic acid. The crude polymers were precipitated in methanol and further purified through Soxhlet extraction in hot methanol, acetone and hexane to remove unreacted starting materials and by-products. The terminal monomers have been functionalized with long and branched 2-ethylhexyl side chains to increase their film-forming abilities.

Top-contact, bottom-gate (TC-BG) architecture OFETs were fabricated as sensor devices. The polymer semiconductors were spin coated from a 10 mg mL$^{-1}$ chloroform solution at 2000 rpm and then was annealed at 120° C. for 10 min in the glovebox. Au source/drain electrodes (W=8000 μm, L=250 μm) were used to measure the electrical performances of PF$_n$ (n=1, 2, 3, 4) devices. The original devices without gas exposure show typical p-type transport.

Sensor Test

Ammonia (4.68 molar concentration) diluted with nitrogen and nitrogen dioxide (49.2 ppm) diluted with nitrogen were purchased from Praxair. The air/gas mixture with various concentrations was introduced into a homemade gas flow test chamber by an Environics 4040 series gas dilution instrument. The air itself was purified by going through a series of purification stages of silica gel, carbon black, deoxy-catalyst, and followed by purafil in order to obtain clean air with minimum contamination of other gases that may hinder or alter measurements. The devices were exposed to each subset of gas concentrations for a total of 3 minutes before measuring. Devices were measured using a 3 point probe station and measured using a Keithley 4200 semiconductor characterization system. The output curves in various concentrations of gas were systematically characterized at VG=−50 V.

Results

A transistor made with poly [3-(3-carboxypropyl)thiophene-2,5-diyl](regioregular) showed an increase of conductance of about 20% after 10 minutes repeated operation in ambient atmosphere, with current output of about 3 microamps from −40 V applied to the drain and gate electrodes, only weakly dependent on the gate voltage. A transistor made with the indolofluorene DPP polymer PF3 showed a decrease in conductance of about 20% at the gate voltage of −80 V and drain voltage of −120 V after 10 minutes repeated operation in ambient atmosphere, with current output of about 0.3 microamps. Making a parallel circuit with a poly [3-(3-carboxypropyl)thiophene-2,5-diyl] (regioregular) device and an indolofluorene device (PF3) with about 30 times the width-to-length (W/L) ratio of the carboxypropylthiophene polymer device, keeping the gate voltages at −40 V and −80 V, respectively, and −120 V applied across the parallel circuit, would lead to a circuit with comparable absolute increase and decrease in conductance, respectively, of the two devices. Thus, current through the series or parallel circuit with voltage applied would drift less than the individual devices would, and this circuit drift could be further decreased with fine adjustments in the W/L ratios and voltages as known in the art.

The response of the poly [3-(3-carboxypropyl)thiophene-2,5-diyl] (regioregular) device to NO$_2$ with concentrations increasing to 1 ppm over 10 minutes is a conductance increase of about a factor of 15. The response of the indolofluorene polymer to a similar exposure is negligible by comparison. Thus, the ratio of current response of the circuit to NO$_2$ and ambient is larger than the ratio of responses of the individual devices to NO$_2$ and ambient.

The response of the poly [3-(3-carboxypropyl)thiophene-2,5-diyl] (regioregular) device to ammonia with concentrations increasing to 0.5 ppm over 10 minutes is a conductance increase of about a factor of 2.5. The response of the indolofluorene polymer to a similar exposure is negligible by comparison. Thus, the ratio of current response of the circuit to ammonia and ambient is larger than the ratio of responses of the individual devices to ammonia and ambient.

A poly[3-(ethyl-4-butanoate)thiophene-2,5-diyl] (regioregular) device showed an increase of conductance of about 20% after 10 minutes repeated operation in ambient atmosphere, weakly gate dependent, with initial current output of about 200 nanoamps with −40 V applied to the drain and gate electrodes. The spirofluorene DPP polymer (PF2) showed a decrease in conductance of about 20% at the gate voltage of −60 V and drain voltage of −120 V after 10 minutes repeated operation in ambient atmosphere, with current output of about 50 nanoamps. Making a parallel circuit with a poly[3-(ethyl-4-butanoate)thiophene-2,5-diyl] (regioregular) device and an indolofluorene device with the latter having twelve times the width-to-length (W/L) ratio, with gate voltages of −60 V on both devices and −120 V across the parallel circuit, would lead to a circuit with comparable absolute increased conductance and decreased conductance of the two devices, respectively. Thus, total current measured in the parallel circuit would drift less than the individual devices would, and this drift could be further decreased with fine adjustments in the W/L ratios and voltages as known in the art.

A second transistor made with the spiro DPP polymer PF2 showed a decrease in conductance of about 10% after 10 minutes repeated operation in ambient atmosphere at the gate and drain voltage of −40 V with current output of about 16 nanoamps. Making a series circuit with a poly[3-(ethyl-4-butanoate)thiophene-2,5-diyl] (regioregular) device and a spiro DPP PF2 device with the latter having a width to length ratio six times that of the former, −40 V on each gate and −80 V across the series circuit will result in comparable absolute conductance increase and decrease of the two devices, respectively. Thus, total current measured in the series circuit would drift less than the individual devices would, and this drift could be further decreased with fine adjustments in the W/L ratios and voltages as known in the art.

A third transistor made with the spiro DPP polymer PF2 showed a decrease in conductance of about 10% after 10 minutes repeated operation in ambient atmosphere at the gate voltage of −40 V and drain voltage of −120 V with current output of about 60 nanoamps. Making a parallel circuit with a poly [3-(ethyl-4-butanoate)thiophene-2,5-diyl] (regioregular) device and a spiro DPP PF2 device with the latter having a width to length ratio five times that of the former, −40 V on each gate and −120 V across the parallel circuit will result in comparable absolute conductance increase and decrease of the two devices, respectively. Thus, total current measured in the parallel circuit would drift less than the individual devices would, and this drift could be further decreased with fine adjustments in the W/L ratios and voltages as known in the art.

The response of the poly[3-(ethyl-4-butanoate)thiophene-2,5-diyl] (regioregular) device to $NO_2$ with concentrations increasing to 1 ppm over about 10 minutes is a conductance increase of about a factor of 20. The response of the indolofluorene or spiro polymer to a similar exposure is negligible by comparison. Thus, the ratio of the current response of the above circuits to $NO_2$ and ambient is larger than the ratio of responses of the individual devices to $NO_2$ and ambient.

The response of the poly[3-(ethyl-4-butanoate)thiophene-2,5-diyl] (regioregular) device to ammonia with concentrations increasing to 0.5 ppm over about 10 minutes is a conductance increase of about a factor of 3.5. The response of the indolofluorene or spiro polymer to a similar exposure is negligible by comparison. Thus, the ratio of the current response of the parallel or series circuits described above to ammonia and ambient is larger than the ratio of responses of the individual devices to $NO_2$ and ambient.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method for detecting a concentration of a vapor analyte in a sample in a presence of an interfering stimulus without the use of a reference sample, the method comprising:
    exposing a single sensor device to the sample, wherein the single sensor device consists of:
        a first organic field effect transistor (OFET) circuit comprising a polymer organic semiconductor molecular structure electronically sensitive to a presence of the vapor analyte and to a presence of the interfering stimulus in the sample;
        a second OFET circuit, comprising the polymer organic semiconductor molecular structure and a chemical modification, electronically sensitive to at least the presence of the interfering stimulus in the sample, wherein the polymer organic semiconductor molecular structure has a different sensitivity to the vapor analyte than the polymer organic semiconductor molecular structure with the chemical modification; and
        at least one conductive link that electrically connects the first OFET circuit and the second OFET circuit in series or parallel,
        wherein the first OFET circuit and the second OFET circuit are concurrently exposed to the sample;
    applying a voltage to the single sensor device exposed to the sample;
    measuring an output voltage at a point within the single sensor device, wherein the concentration of the vapor analyte in the sample is indicated by a voltage change from the applied voltage to the output voltage, wherein the output voltage is based on:
        a first electrical signal from the first OFET circuit being electronically sensitive to the presence of the vapor analyte and to the presence of the interfering stimulus,
        a second electrical signal from the second OFET circuit being electronically sensitive to at least the presence of the interfering stimulus, and
        a portion of the first electrical signal and a portion of the second electrical signal cancelling each other out to eliminate a response to the interfering stimulus; and
    providing, by the sensor device, an output indicative of the concentration of the vapor analyte in the sample that does not depend on the presence of the interfering stimulus.

2. The method of claim 1, wherein the portion of the first electrical signal and the portion of the second electrical signal cancelling each other out results in increased selectivity in detecting the concentration of the vapor analyte.

3. The method of claim 1, wherein the portion of the first electrical signal and the portion of the second electrical signal cancel each other out as a ratio or a summation.

4. The method of claim 1, wherein the interfering stimulus is an interfering chemical species, a temperature change, a humidity, a water vapor, an electromagnetic energy, and/or a mechanical force.

5. The method of claim 1, wherein the first OFET circuit has a different change in electrical conductance than the second OFET circuit in response to sensing at least one of the vapor analyte and the interfering stimulus.

6. The method of claim 1, further comprising:
applying, by a light source, a compensatory light to the first OFET circuit and the second OFET circuit to stabilize the first OFET circuit and the second OFET circuit to reduce noise in the output.

7. The method of claim 1, wherein the sample comprises a plurality of molecules.

8. The method of claim 1, wherein the first OFET and the second OFET share a common gate electrode.

9. The method of claim 1, wherein the conductive link is a gallium-indium paste and/or a silver paste.

10. The method of claim 1, wherein the polymer organic semiconductor molecular structure comprises a thiophene-based backbone.

11. The method of claim 10, wherein the chemical additive comprises at least one sulfide group adjacent to at least one thiophene ring of the thiophene-based backbone.

12. The method of claim 1, wherein the polymer organic semiconductor molecular structure comprises deep traps controlling a voltage and shallow traps limiting a charge carrier mobility.

* * * * *